United States Patent
Sakaida

(10) Patent No.: US 7,424,173 B2
(45) Date of Patent: *Sep. 9, 2008

(54) METHOD, APPARATUS AND PROGRAM FOR RESTORING PHASE INFORMATION

(75) Inventor: Hideyuki Sakaida, Kaisei-machi (JP)

(73) Assignee: FUJIFILM Corporation, Tokyo (JP)

(*) Notice: Subject to any disclaimer, the term of this patent is extended or adjusted under 35 U.S.C. 154(b) by 726 days.

This patent is subject to a terminal disclaimer.

(21) Appl. No.: 10/671,786

(22) Filed: Sep. 29, 2003

(65) Prior Publication Data

US 2004/0062452 A1    Apr. 1, 2004

(30) Foreign Application Priority Data

Sep. 30, 2002  (JP)  ............................ 2002-285252
Oct. 7, 2002   (JP)  ............................ 2002-293740

(51) Int. Cl.
    *G06K 9/64*  (2006.01)
(52) U.S. Cl. ...................... 382/276; 382/279
(58) Field of Classification Search ................ 382/132, 382/299, 274; 359/634, 722; 356/320, 925, 356/939; 378/98.9
    See application file for complete search history.

(56) References Cited

U.S. PATENT DOCUMENTS

| | | | | |
|---|---|---|---|---|
| 5,361,291 A | * | 11/1994 | Toth et al. | 378/12 |
| 5,802,137 A | * | 9/1998 | Wilkins | 378/85 |
| 6,226,353 B1 | * | 5/2001 | Wilkins et al. | 378/98.9 |
| 7,171,031 B2 | * | 1/2007 | Sakaida | 382/128 |
| 2001/0048744 A1 | | 12/2001 | Kimura | |
| 2002/0110123 A1 | | 8/2002 | Shitama | |
| 2002/0176615 A1 | * | 11/2002 | Ito | 382/132 |
| 2003/0199752 A1 | * | 10/2003 | Sakaida | 600/410 |

FOREIGN PATENT DOCUMENTS

| | | |
|---|---|---|
| EP | A2-1 161 031 | 12/2001 |
| EP | A3-1 161 031 | 12/2001 |
| JP | 2001-506160 A | 5/2001 |
| JP | 2001-170034 A | 6/2001 |

(Continued)

OTHER PUBLICATIONS 0031-9007/96/2961-2964 The american Physical society. Quantitative Phase Imaging Using Hard X-Rays.*

(Continued)

*Primary Examiner*—Yosef Kassa
*Assistant Examiner*—Jayesh A Patel
(74) *Attorney, Agent, or Firm*—Sughrue Mion, PLLC

(57) ABSTRACT

A phase information restoring method improves estimation accuracy of phase by using radiation with energy of high transmittance when constructing a radiation image of a living organism such as a human body by the phase-contrast method. The phase information restoring method includes the steps of: (a) obtaining plural sets of detection data respectively representing plural kinds of radiation image information on a detection plane at a predetermined distance from an object by using plural radiations having different wavelengths with energy from 16 keV to 30 keV to detect intensity of the plural radiations transmitted through the object on the detection plane; and (b) restoring phase information on the radiations transmitted through the object on the basis of the plural sets of detection data so as to obtain phase data.

4 Claims, 22 Drawing Sheets

FOREIGN PATENT DOCUMENTS

| | | |
|---|---|---|
| JP | A-2001-345819 | 12/2001 |
| JP | A-2002-152279 | 5/2002 |
| WO | 98/28950 A1 | 7/1998 |

OTHER PUBLICATIONS

B.E. Allman, et al. "Noninterferometric Quantitative Phase Imaging with Soft X Rays" J. Opt. Soc. Am. A/vol. 17, No. 10/Oct. 2000.

T.E. Gureyev, et al. "Hard X Ray Quantitative Non-Interferometric Phase-Contrast Imaging", Part of SPIE Conference on Physics of Medical Imaging, Feb. 1999.

T.E. Gureyev, et al. "Quantitative In-Line Phase-Contrast Imaging with Multienergy X Rays", Physics Review Letters, vol. 86, No. 25, Jun. 18, 2001.

* cited by examiner

FIG.22
PRIOR ART
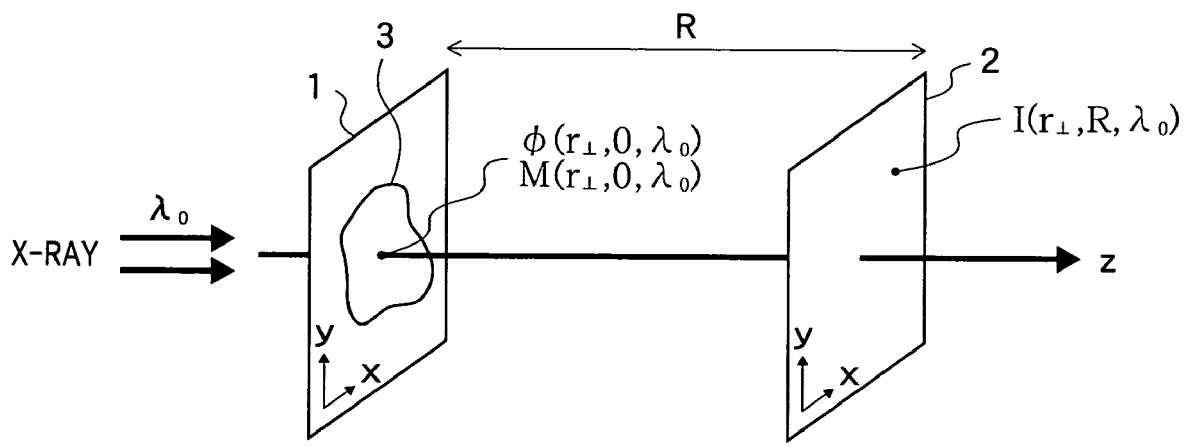
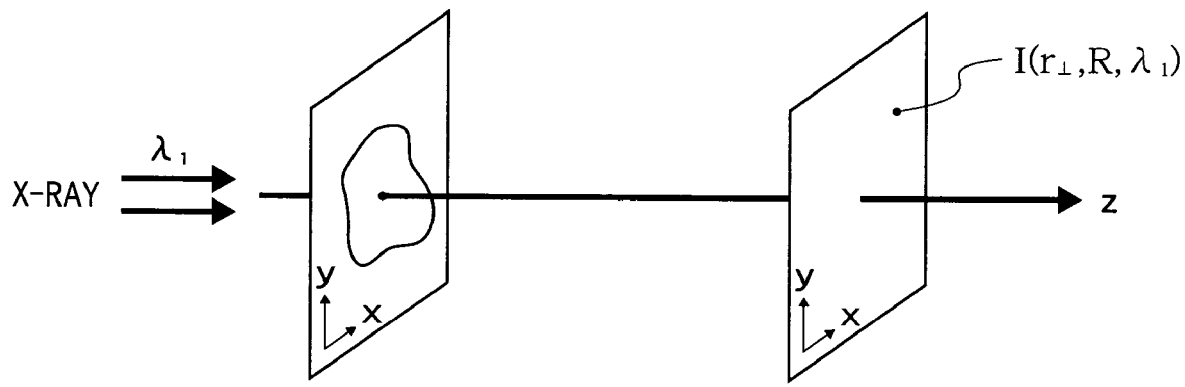
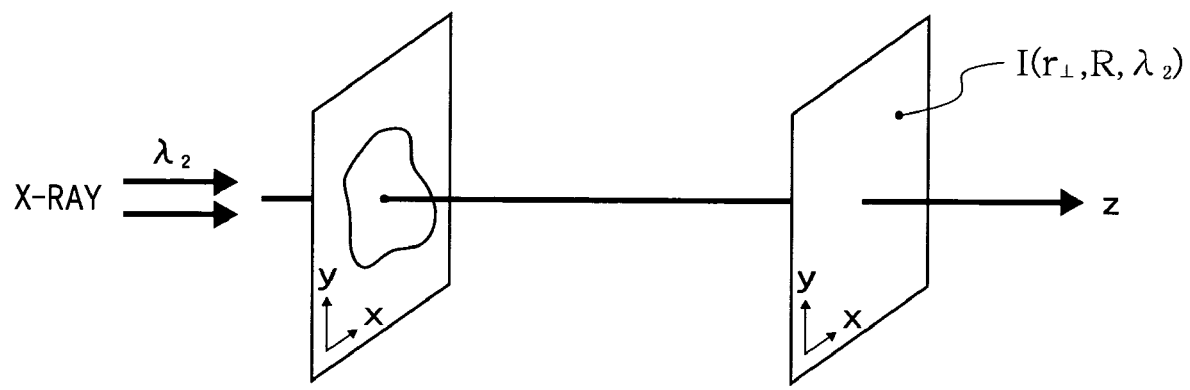

METHOD, APPARATUS AND PROGRAM FOR RESTORING PHASE INFORMATION

BACKGROUND OF THE INVENTION

1. Field of the invention

The present invention relates to a method, an apparatus, and a program for restoring phase information to be used for constructing an image on the basis of image information obtained by radiation imaging. In this application, the word "radiation" is used in a broad sense that includes corpuscular beams such as an electron beam, and electromagnetic waves, in addition to X-rays, α-rays, β-rays, γ-rays, ultraviolet rays and the like.

2. Description of a Related Art

Conventionally, an imaging method using an X-ray, etc. is utilized in various fields, and particularly in the medical field, the method is one of the most important means for diagnosis. Since the first X-ray photograph was implemented, the X-ray photography method has been repeatedly improved, and a method using a combination of a fluorescent screen and an X-ray film is in the mainstream at present. On the other hand, in recent years, various digitized devices applying X-ray CT, ultrasonic waves, MRI, etc. are in practical use, and construction of a diagnostic information processing system or the like in hospitals is being promoted. With respect to X-ray images, many studies are also made for digitizing the imaging system. Digitizing the imaging system enables to store a large amount of data for a long period without degradation in image quality, and helps to make progress toward the medical diagnostic information processing system.

Now, a radiation image obtained as described above is generated by converting intensity of the radiation transmitted through an object into brightness of the image. For example, when performing imaging on a region including a bone part, the radiation transmitted through the bone part is largely attenuated, and the radiation transmitted through a region other than the bone part, i.e., a soft part is slightly attenuated. In this case, since the difference in intensity between the radiations transmitted through different tissues is large, a high-contrast radiation image can be obtained.

On the other hand, for example, when imaging a region of the soft part such as a breast, since radiation is easily transmitted through the soft part as a whole, the difference between tissues in the soft part is difficult to appear as the difference in intensity of the transmitted radiation. Therefore, only a low-contrast radiation image can be obtained with respect to the soft part. Thus, the conventional radiation imaging method is not suitable as a method of visualizing the slight difference between tissues in the soft part.

Here, as information included in the radiation transmitted through the object, there is phase information in addition to intensity information. Recently, a phase-contrast method of generating an image using this phase information is under study. The phase-contrast method is an image construction technology to convert phase difference produced by an X-ray, etc. transmitted through the object into brightness of an image.

The phase-contrast method includes a technique for obtaining phase difference on the basis of interference X-ray produced by using an interferometer or a zone plate, and a technique for obtaining phase difference on the basis of diffraction X-ray. Among these techniques, the technique for obtaining phase difference on the basis of diffraction X-ray (diffraction technique) is to obtain phase difference on the basis of the following principle. An X-ray, for example, propagates within a material because a wave progresses similarly to light. The propagation rate varies according to the refraction index of the material. Therefore, when applying an X-ray having uniform phase toward the object, the propagation rate of the X-ray varies according to the difference between tissues in the object. Thereby, the wavefront of the X-ray transmitted through the object is distorted and, as a result, diffraction fringes are produced in the X-ray image obtained on the basis of the transmitted X-ray. The pattern of the diffraction fringes differs in accordance with the distance between the screen on which the X-ray image is formed and the object, and the wavelength of the X-ray. Thus, analyzing two or more X-ray images having different patterns of diffraction fringes, phase differences of the X-ray generated in the respective positions on the screen can be obtained. By converting the phase differences into brightness, an X-ray image that clearly shows the difference between tissues in the object can be obtained.

Particularly, in the radiation after transmitted through a soft part of the object, since the difference in phase is larger than the difference in intensity in accordance with the difference between tissues through which the radiation has been transmitted, the subtle difference between tissues can be visualized by using the phase-contrast method. In order to use the above-described phase-contrast method, imaging conditions in radiation imaging or techniques for restoring phase information from patterns of diffraction fringes are under study.

B. E. Allman et al. "Noninterferometric quantitative phase imaging with soft x rays", J. Optical Society of America A, Vol. 17, No. 10 (October 2000), pp. 1732-1743 discloses that an X-ray image is constructed by performing phase restoration on the basis of image information obtained by imaging with soft X-rays. In this reference, the basic equation of phase restoration, TIE (transport of intensity equation) is used.

$$\kappa \frac{\partial I(r)}{\partial z} = -\nabla_\perp \cdot \{I(r)\nabla_\perp \phi(r)\} \quad (1)$$

Where r=(x, y, z) is vector, and $$\nabla_\perp = \left(\frac{\partial}{\partial x}, \frac{\partial}{\partial y}\right)$$

In addition, κ denotes wave number.

Next, a principle of the phase restoration will be described by referring to FIG. 21. As shown in FIG. 21, an X-ray having a wavelength λ is input from the left side of the drawing, transmitted through an object plane 1 and enters a screen 2 at a distance of z from the object plane 1. Here, assuming that the intensity and the phase of the X-ray in a position (x, y) on the screen 2 are I(x, y) and φ(x, y), respectively. In this case, relationship expressed by the following equation holds between the intensity I(x, y) and phase φ(x, y). Here, the intensity I is square of amplitude of wave.

$$\frac{2\pi}{\lambda} \frac{\partial I(x, y)}{\partial z} = -\nabla \cdot \{I(x, y)\nabla \phi(x, y)\} \quad (2)$$

Substituting κ=2π/λ into Eq. (2) and rewriting (x, y) components into vector r, TIE expressed by Eq. (1) is derived.

However, since the above TIE is difficult to be solved, TIE has been used mainly by performing approximation thereon.

For example, T. E. Gureyev et al. "Hard X-ray quantitative non-interferometric phase-contrast imaging", SPIE, Vol. 3659 (1999), pp. 356-364 discloses that an X-ray image is constructed by performing phase restoration on the basis of image information obtained by imaging with hard X-rays. In this reference, TIE expressed by Eq. (1) is approximated as follows. First, Eq. (1) is developed. In the following equations, the vector r in the above reference is rewritten into (x, y) components.

$$-\kappa \frac{\partial I(x,y)}{\partial z} = \left(\frac{\partial}{\partial x}, \frac{\partial}{\partial y}\right) \cdot \left(I(x,y)\frac{\partial \phi(x,y)}{\partial x}, I(x,y)\frac{\partial \phi(x,y)}{\partial y}\right) \quad (3)$$

$$= \frac{\partial}{\partial x}\left(I(x,y)\frac{\partial \phi(x,y)}{\partial x}\right) + \frac{\partial}{\partial y}\left(I(x,y)\frac{\partial \phi(x,y)}{\partial y}\right)$$

$$= I(x,y)\left(\frac{\partial^2 \phi(x,y)}{\partial x^2} + \frac{\partial^2 \phi(x,y)}{\partial y^2}\right) +$$

$$\frac{\partial I(x,y)}{\partial x}\frac{\partial \phi(x,y)}{\partial x} + \frac{\partial I(x,y)}{\partial y}\frac{\partial \phi(x,y)}{\partial y}$$

$$= I(x,y)\nabla^2 \phi(x,y) + \nabla I(x,y) \cdot \nabla \phi(x,y)$$

Where $$\nabla^2 = \frac{\partial^2}{\partial x^2} + \frac{\partial^2}{\partial y^2}$$

Approximating the second term on the right side of Eq. (3) to zero, the approximation equation expressed by the following equation (4) is obtained.

$$\frac{\partial I(x,y)}{\partial z} \cong -\frac{I(x,y)}{\kappa}\nabla^2 \phi(x,y) \quad (4)$$

In Eq. (4), $\phi(x, y)$ can be obtained from $I(x, y)$ by a solution method such as the finite element method.

In addition, T. E. Gureyev et al. "Quantitative In-Line Phase-Contrast Imaging with Multienergy X Rays", Physical Review Letter, Vol. 86, No. 25 (2001), PP. 5827-5830 discloses that an X-ray imaging is performed by using three kinds of X-rays having different wavelengths and the phase restoration is performed on the basis of the obtained image information. In this reference, attention is given to the relationship between phase and intensity of the X-ray just after transmitted through the object and intensity of the X-ray in a position at a predetermined distance from the object. When performing the X-ray imaging, the structure shown in FIG. 22 is assumed. That is, as shown in FIG. 22, the three kinds of X-rays having wavelengths $\lambda_0$, $\lambda_1$, and $\lambda_2$, respectively, are transmitted through the object 3, and enter the screen 2 that is disposed in a position at a distance R from the object plane 1.

In this case, assuming that $r_\perp = (x, y)$, the following relationship is held between the intensity $I(r_\perp, 0, \lambda_0)$ and the phase $\phi(r_\perp, 0, \lambda_0)$ of the X-ray of wavelength $\lambda_0$, which is just after transmitted through the object 3, and the intensity $I(r_\perp, R, \lambda_m)$ of the diffraction X-ray of wavelength $\lambda_m$ which is detected on the screen 2. In the following Equation (5), $I(r_\perp, 0, \lambda_0) = \exp\{-M(r_\perp, 0, \lambda_0)\}$.

$$A\begin{pmatrix} M(r_\perp, 0, \lambda_0) \\ -\nabla^2 \phi(r_\perp, 0, \lambda_0) \\ \nabla M \cdot \nabla \phi(r_\perp, 0, \lambda_0) \end{pmatrix} = \begin{pmatrix} g_0 \\ g_1 \\ g_2 \end{pmatrix} \quad (5)$$

Where, $$A = \begin{pmatrix} -1 & \gamma_0 & \gamma_0 \\ -\sigma_1^3 & \sigma_1\gamma_1 & \sigma_1^4\lambda_1 \\ -\sigma_2^3 & \sigma_2\gamma_2 & \sigma_2^4\lambda_2 \end{pmatrix}$$

$$\sigma_m = \frac{\lambda_m}{\lambda_0}, \gamma_m = \frac{R\lambda_m}{2\pi}, g_m = \ln\{I(r_\perp, R, \lambda_m)\} \ (m = 0, 1, 2)$$

In Eq. (5), if $\nabla M \cdot \nabla \phi(r_\perp, R, \lambda_0)$ is sufficiently small, approximation can be as follows.

$$\begin{pmatrix} -1 & \gamma_0 \\ -\sigma_1^3 & \sigma_1\gamma_1 \end{pmatrix}\begin{pmatrix} M(r_\perp, 0, \lambda_0) \\ -\nabla^2 \phi(r_\perp, 0, \lambda_0) \end{pmatrix} = \begin{pmatrix} g_0 \\ g_1 \end{pmatrix} \quad (6)$$

Further, from Eq. (6), the intensity and the phase of the X-ray just after transmitted through the object 3 are expressed as follows.

$$M(r_\perp, 0, \lambda_0) = \frac{\lambda}{\Delta\lambda}(g_0 - \sigma^{-2}g_1) \quad (7)$$

$$-\nabla^2 \phi(r_\perp, 0, \lambda_0) = \frac{2\pi}{R\Delta\lambda}(\sigma g_0 - \sigma^{-2}g_1) \quad (8)$$

Where, $\Delta\lambda = \lambda_1 - \lambda_0$ and $\sigma \equiv \sigma_1 = \lambda_1/\lambda_0$.

The phase $\phi(r_\perp, R, \lambda_0)$ can be obtained by performing inverse Laplacian computation on the Laplacian $\nabla^2 \phi(r_\perp, R, \lambda_0)$ of the phase in Eq. (8). Further, a visible image representing the object can be obtained by converting this phase into brightness in the image. Thus, by using Eq. (8), the computation for phase restoration can be easily performed on the basis of a small number of irradiation images obtained by changing the wavelengths. Therefore, in T. E. Gureyev et al. "Quantitative In-Line Phase-Contrast Imaging with Multienergy X Rays", Physical Review Letter, Vol. 86, No. 25 (2001), pp. 5827-5830, X-ray imaging is performed by using X-rays having three kinds of wavelengths (energy) $\lambda_0 = 3.8$ Å ($E_0 = 3.3$ keV), $\lambda_1 = 7.3$ Å ($E_1 = 1.7$ keV), and $\lambda_2 = 2.5$ Å ($E_2 = 5.0$ keV).

Although a thin object can be imaged at these wavelengths, there is a problem that the imaging method is unsuitable in the case where an object having a larger thickness such as a breast or a chest of a human body is to be imaged because X-ray absorption when transmitted through the object is too large at these wavelengths.

Further, in order to perform higher precision phase restoration, it is desired to use a high-definition (high resolution) screen constituted by a many number of detecting elements the size of which is made as small as possible.

However, in the case where the high-definition screen is used, there is a problem that the X-ray imaging becomes vulnerable to the influence of noise. In order to reduce the influence of noise, it is conceivable that the irradiation amount of X-ray is increased. However, in the case of a living organism such as a human body, there is a problem that the irradiation amount can not be increased for fear of exposure. By the way, in the above-described papers of B. E. Allman et al. and T. E. Gureyev et al. in which a non-living organism is imaged, the relationship between noise and irradiation amount is not described.

SUMMARY OF THE INVENTION

The present invention has been achieved in view of the above-described problems. A first object of the present invention is to provide a phase information restoring method that enables to improve estimation accuracy of phase by using radiation with energy of high transmittance when constructing a radiation image of a living organism such as a human body by the phase-contrast method. Additionally, a second object of the present invention is to provide a phase information restoring method in which the influence of noise can be reduced without increasing irradiation amount of X-rays. Further a third object of the present invention is to provide a phase information restoring apparatus and a phase information restoring program for using these phase information restoring methods.

In order to solve the above described problems, a phase information restoring method according to a first aspect of the present invention is a method of restoring phase information on radiations transmitted through an object on the basis of detection data obtained by detecting intensity of the radiations transmitted through the object. The method comprises the steps of: (a) obtaining plural sets of detection data respectively representing plural kinds of radiation image information on a detection plane at a predetermined distance from the object by using plural radiations having different wavelengths with energy from 16 keV to 30 keV to detect intensity of the plural radiations on the detection plane; and (b) restoring phase information on the radiations transmitted through the object on the basis of the plural sets of detection data so as to obtain phase data.

Further, a phase information restoring method according to a second aspect of the present invention is a method of restoring phase information on a radiation transmitted through an object on the basis of detection data obtained by detecting intensity of the radiation transmitted through the object. The method comprises the steps of: (a) obtaining plural sets of detection data respectively representing plural kinds of radiation image information on plural detection planes at different distances from the object by using a radiation having a predetermined wavelength with energy from 16 keV to 30 keV to detect intensity of the radiation on the plural detection planes; and (b) restoring phase information on the radiation transmitted through the object on the basis of the plural sets of detection data so as to obtain phase data.

Furthermore, a phase information restoring method according to a third aspect of the present invention is a method of restoring phase information on a radiation transmitted through an object on the basis of detection data obtained by detecting intensity of the radiation emitted from a radiation source having a focal spot size $\sigma$ in a position at a distance R from the object and transmitted through the object. The method comprises the steps of: (a) obtaining plural sets of detection data respectively representing plural kinds of radiation image information on plural detection planes at different distances $z_i$ from the object by using a radiation detector for detecting intensity of applied radiation on the plural detection planes to generate a detection signal representing radiation image information in which a pixel size is not less than $\pi\sigma z/3R$, where z is a maximum value of $z_i$; and (b) restoring phase information on the radiation transmitted through the object on the basis of the plural sets of detection data so as to obtain phase data.

Moreover, a phase information restoring method according to a fourth aspect of the present invention is a method of restoring phase information on a radiation transmitted through an object on the basis of detection data obtained by detecting intensity of the radiation emitted from a radiation source having a focal spot size $\sigma$ in a position at a distance R from the object and transmitted through the object. The method comprises the steps of: (a) acquiring plural sets of first detection data respectively representing plural kinds of radiation image information on plural detection planes at different distances $z_i$ from the object and obtained by detecting intensity of the radiation on the plural detection planes; (b) respectively generating plural sets of second detection data by suppressing spatial frequency components larger than $3R/2\pi\sigma z$ with respect to the plural sets of first detection data, where z is a maximum value of $z_i$; and (c) restoring phase information on the radiation transmitted through the object on the basis of the plural sets of second detection data so as to obtain phase data.

A phase information restoring apparatus according to a first aspect of the present invention is an apparatus for restoring phase information on radiations transmitted through an object on the basis of detection data obtained by detecting intensity of the radiations transmitted through the object. The apparatus comprises: a radiation source for emitting each of plural radiations having different wavelengths with energy from 16 keV to 30 keV; detecting means for detecting intensity of the radiation emitted from the radiation source and transmitted through the object so as to obtain detection data representing radiation image information; and phase data calculating means for restoring phase information on the radiations having different wavelengths and transmitted through the object on the basis of plural sets of detection data obtained by detecting intensity of the plural radiations so as to obtain phase data.

Further, a phase information restoring apparatus according to a second aspect of the present invention is an apparatus for restoring phase information on a radiation transmitted through an object on the basis of detection data obtained by detecting intensity of the radiation transmitted through the object. The apparatus comprises: a radiation source for emitting a radiation having a predetermined wavelength with energy from 16 keV to 30 keV; detecting means for detecting intensity of the radiation emitted from the radiation source and transmitted through the object so as to obtain detection data representing radiation image information; driving means to be used for changing a distance between the object and the detecting means; and phase data calculating means for restoring phase information on the radiation transmitted through the object on the basis of plural sets of detection data obtained by detecting intensity of the radiation at different distances so as to obtain phase data.

Furthermore, a phase information restoring apparatus according to a third aspect of the present invention is an apparatus for restoring phase information on a radiation transmitted through an object on the basis of detection data obtained by detecting intensity of the radiation, which has been emitted from a radiation source having a focal spot size $\sigma$ in a position at a distance R from the object and transmitted through the object, on plural detection planes at different distances $z_i$ from the object. The apparatus comprises: detecting means for detecting intensity of applied radiation so as to obtain detection data representing radiation image information in which a pixel size is not less than $\pi\sigma z/3R$, where z is a maximum value of $z_i$; and phase data calculating means for restoring phase information on the radiation transmitted through the object on the basis of plural sets of detection data obtained by detecting intensity of the radiation transmitted at different distances $z_i$ so as to obtain phase data.

Moreover, a phase information restoring apparatus according to a fourth aspect of the present invention is an apparatus for restoring phase information on a radiation transmitted through an object on the basis of detection data obtained by detecting intensity of the radiation, which has been emitted from a radiation source having a focal spot size σ in a position at a distance R from the object and transmitted through the object, on plural detection planes at different distances $z_i$ from the object. The apparatus comprises: signal processing means for respectively generating plural sets of second detection data by suppressing spatial frequency components larger than $3R/2\pi\sigma z$ with respect to plural sets of first detection data obtained by detecting intensity of the radiation at different distances $z_i$, where z is a maximum value of $z_i$; and phase data calculating means for restoring phase information on the radiation transmitted through the object on the basis of the plural sets of second detection data generated by the signal processing means so as to obtain phase data.

A phase information restoring program according to a first aspect of the present invention is a program for restoring phase information on radiations transmitted through an object on the basis of detection data obtained by emitting the radiations from a radiation source and detecting intensity of the radiation transmitted through the object. The program actuates a CPU to execute the procedures of: controlling the radiation source to emit each of radiations having different wavelengths with energy from 16 keV to 30 keV; obtaining a Laplacian of phase on the basis of plural sets of detection data obtained by detecting intensity of the radiations having different wavelengths; and obtaining phase data of the radiation by performing inverse Laplacian computation on the Laplacian of phase.

Further, a phase information restoring program according to a second aspect of the present invention is a program for restoring phase information on a radiation transmitted through an object on the basis of detection data obtained by emitting the radiation from a radiation source and detecting intensity of the radiation transmitted through the object. The program actuates a CPU to execute the procedures of: controlling the radiation source to emit a radiation having a predetermined wavelength with energy from 16 keV to 30 keV; obtaining a Laplacian of phase on the basis of plural sets of detection data obtained by detecting intensity of the radiation at different distances; and obtaining phase data of the radiation by performing inverse Laplacian computation on the Laplacian of phase.

Furthermore, a phase information restoring program according to a third aspect of the present invention is a program for restoring phase information on a radiation transmitted through an object on the basis of detection data obtained by detecting intensity of the radiation emitted from a radiation source having a focal spot size σ in a position at a distance R from the object and transmitted through the object. The program actuates a CPU to execute the procedures of: obtaining plural sets of detection data respectively representing plural kinds of radiation image information on plural detection planes at different distances $z_i$ from the object by using a radiation detector for detecting intensity of applied radiation on the plural detection planes to generate a detection signal representing radiation image information in which a pixel size is not less than $\pi\sigma z/3R$, where z is a maximum value of $z_i$; and obtaining a Laplacian of phase on the basis of the plural sets of detection data; and obtaining phase data of the radiation by performing inverse Laplacian computation on the Laplacian of phase.

Moreover, a phase information restoring program according to a fourth aspect of the present invention is a program for restoring phase information on a radiation transmitted through an object on the basis of detection data obtained by detecting intensity of the radiation emitted from a radiation source having a focal spot size σ in a position at a distance R from the object and transmitted through the object. The program actuates a CPU to execute the procedures of: acquiring plural sets of first detection data obtained by detecting intensity of the radiation on plural detection planes at different distances $z_i$ from the object; respectively generating plural sets of second detection data by suppressing spatial frequency components larger than $3R/2\pi\sigma z$ with respect to the plural sets of first detection data, where z is a maximum value of $z_i$; obtaining a Laplacian of phase on the basis of the plural sets of second detection data; and obtaining phase data of the radiation by performing inverse Laplacian computation on the Laplacian of phase.

According to the first and second aspects of the present invention, when constructing the radiation image of a living organism such as a human body by the phase-contrast method, the estimation accuracy of phase can be improved by using radiation with energy of high transmittance. Further, according to the third and fourth aspects of the present invention, the influence of noise can be reduced without increasing irradiation amount of the X-ray by suppressing the predetermined spatial frequency component.

BRIEF DESCRIPTION OF THE DRAWINGS

FIG. 22 is a diagram for explanation of a principle of phase restoration.

DESCRIPTION OF THE PREFERRED EMBODIMENTS

Figure 1:
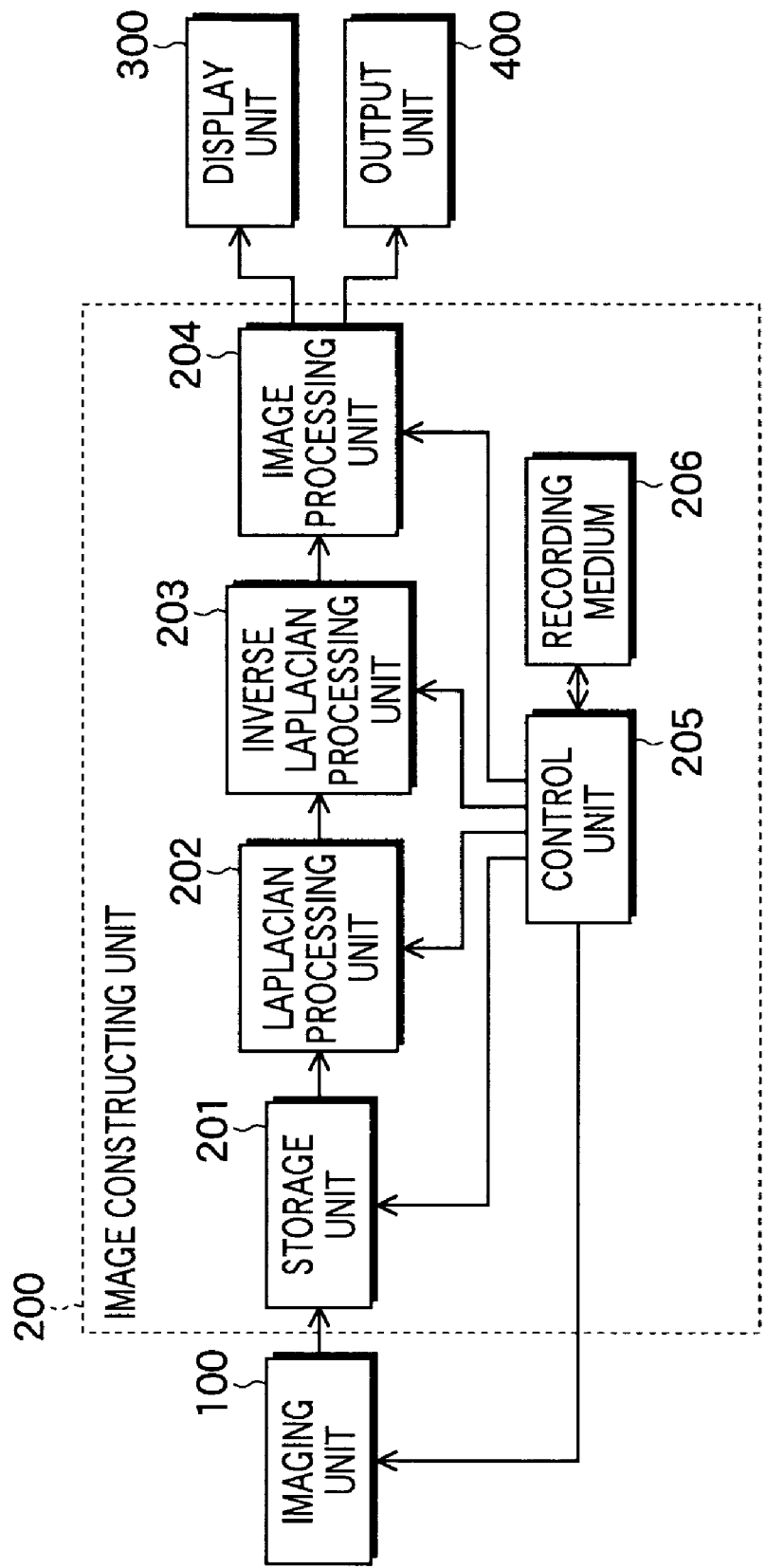
FIG. 1 is a block diagram showing a constitution of a phase information restoring apparatus according to a first embodiment of the present invention.

Now, referring to the drawings, embodiments of the present invention will be described in detail. The same component elements will be given with the same reference numerals and the descriptions thereof will be omitted.

FIG. 1 is a block diagram showing a constitution of a phase information restoring apparatus according to a first embodiment of the present invention. As shown in FIG. 1, this phase information restoring apparatus has an imaging unit 100 for outputting detection data that represents radiation image information on an object by applying x-rays to the object, an image constructing unit 200 for generating image data by restoring phase information on the basis of the detection data, a display unit 300 for displaying a visible image on the basis of the image data, and an output unit 400 for printing out the visible image on a film, etc.

Figure 2:
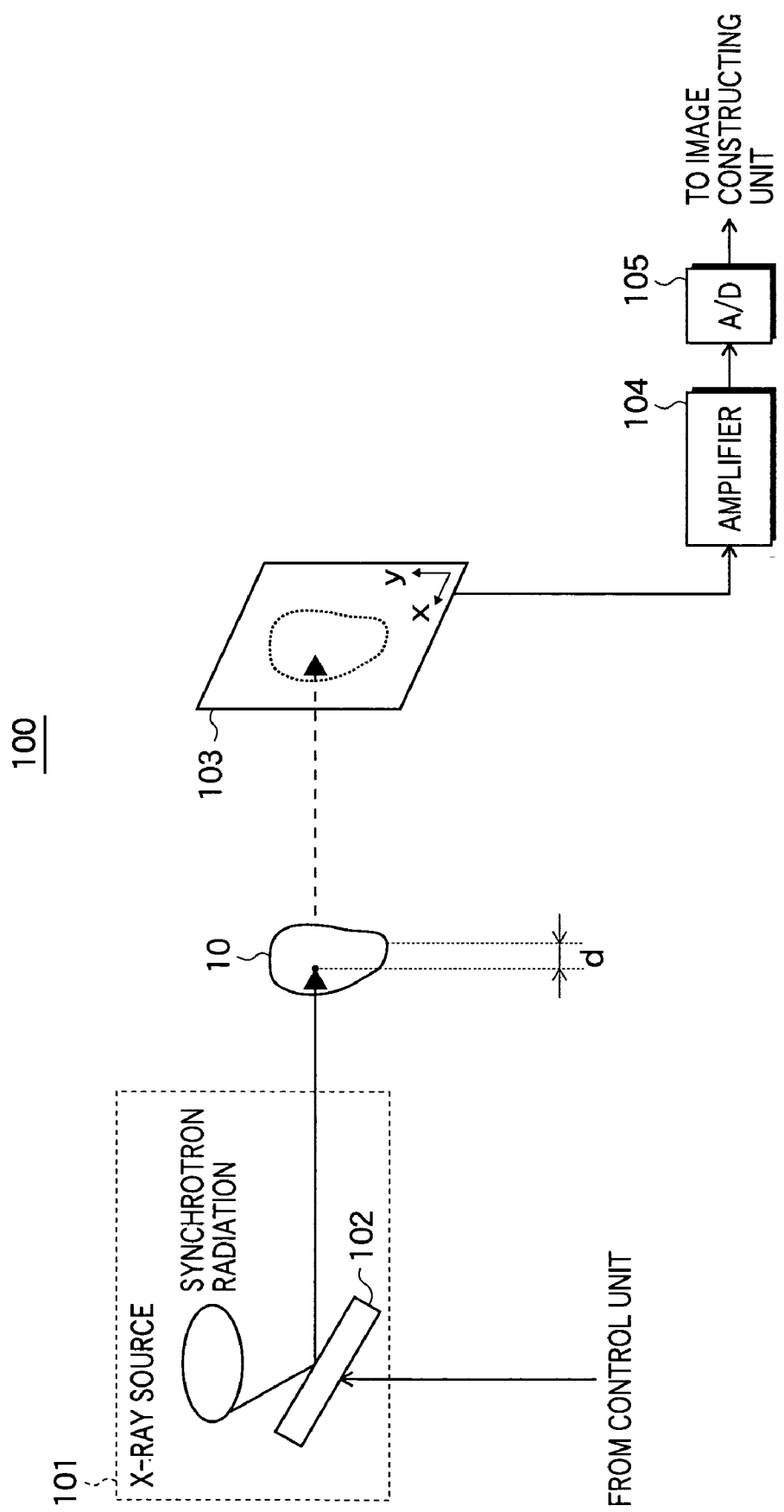
FIG. 2 is a diagram showing a constitution of an imaging unit shown in FIG. 1.

FIG. 2 is a diagram showing a constitution of the imaging unit 100. The imaging unit 100 includes an X-ray source 101, a monochromator 102, and a sensor 103.

As the X-ray source, it is desirable to use one capable of generating a beam that is highly coherent and monochromatic. Here, the highly monochromatic beam indicates a beam that mainly has single wavelength. However, it is unnecessary that the beam strictly has single wavelength. For this purpose, in the embodiment, the X-ray source 101 including a synchrotron radiation source for generating synchrotron radiation and the monochromator 102 is used. By extracting a predetermined wavelength component of an X-ray included in the synchrotron radiation by using the monochromator 102, a monochromatic X-ray is obtained. In the embodiment, as described later, two kinds of X-rays having wavelengths $\lambda_0$ and $\lambda_1$ respectively are obtained. The synchrotron radiation represents radiation (electromagnetic wave) that is generated by circularly or spirally moving an electron in magnetic field, and has wide range continuous spectrum including an X-ray region. In the synchrotron radiation source generating such synchrotron radiation, a wavelength component included in the synchrotron radiation can be changed by varying centripetal acceleration of an electron.

As shown in FIG. 2, the X-ray generated from the X-ray source 101 is transmitted through the object 10 and enter the sensor 103 to produce diffraction fringes. Hereinafter, a distance between the object 10 and the sensor 103 is referred to as "imaging distance".

The sensor 103 is used as a screen for causing the X-ray to enter and produce diffraction fringes, and outputs detection signals representing intensity of diffraction X-ray entering the respective positions of the sensor 103. As the sensor 103, a two-dimensional sensor such as a CCD (charge coupled device) is used, which has a plurality of detecting elements that convert intensity of the incident X-rays into electric signals and output the signals.

Further, the imaging unit 100 includes an amplifier 104 and an A/D converter 105. The amplifier 104 amplifies the detection signal outputted from the sensor 103. The A/D converter 105 converts the detection signal amplified by the amplifier 104 into a digital signal (referred to as "image signal" or "detection data") and outputs it to the image constructing unit 200.

Referring to FIG. 1 again, the image constructing unit 200 has a storage unit 201 for temporarily storing the detection data outputted from the imaging unit 100, a Laplacian processing unit 202 for calculating a value that corresponds to a Laplacian of phase on the basis of the two pieces of detection data obtained by the two kinds of X-rays having different wavelengths at the same imaging distance, an inverse Laplacian processing unit 203 for performing inverse Laplacian computation for phase restoration, an image processing unit 204 for generating image data on the basis of the restored phase information, and a control unit 205 for controlling the respective units 201-204 and wavelengths of the X-rays in the imaging unit 100. The image constructing unit 200 may be configured with a digital circuit or software and a CPU. In the latter case, the control unit 205 including the CPU processes the detection data on the basis of a phase information restoring program recorded on a recording medium 206. As the recording medium 206, a flexible disk, a hard disk, an MO, an MT, a RAM, a CD-ROM, a DVD-ROM, etc. are applicable.

The display unit 300 is a display device such as a CRT, for example, and displays a visible image on the basis of the image data that represents the phase information restored by the image constructing unit 200. Further, the output unit 400 is a laser printer, for example, and prints out the visible image on a film, etc. on the basis of the image data.

Next, the relationship between the wavelength (energy) of the X-ray generated in the X-ray source 101 and transmittance in the object 10 will be described. Here, the object 10 is assumed to have a thickness d, as shown in FIG. 2. Expressing the thickness of the object as d, and refraction index as $n=1-\delta-i\beta$ (i is an imaginary unit), the X-ray $\phi_{OUT}$ just after transmitted through the object is expressed as follows by using the X-ray $\phi_{IN}$ just before transmitted through the object 10.

$$\phi_{OUT} = \phi_{IN} e^{-iknd} = \phi_{IN} e^{-k\beta d} e^{-ik(1-\delta)d} \quad (9)$$

Where, assuming the wavelength of the X-ray as $\lambda$, an equation $k=2\pi/\lambda$ stands up.

Therefore, the intensity $I_{OUT}$ of the X-ray just after transmitted through the object 10 is expressed as follows by using the $I_{IN}$ of the X-ray just before transmitted through the object 10.

$$I_{OUT} = |\phi_{OUT}|^2 = |\phi_{IN}|^2 e^{-2k\beta d} = I_{IN} e^{-2k\beta d} \quad (10)$$

Accordingly, the transmittance T is expressed as follows.

$$T = \frac{I_{OUT}}{I_{IN}} = e^{-2k\beta d} \quad (11)$$

Figure 3:
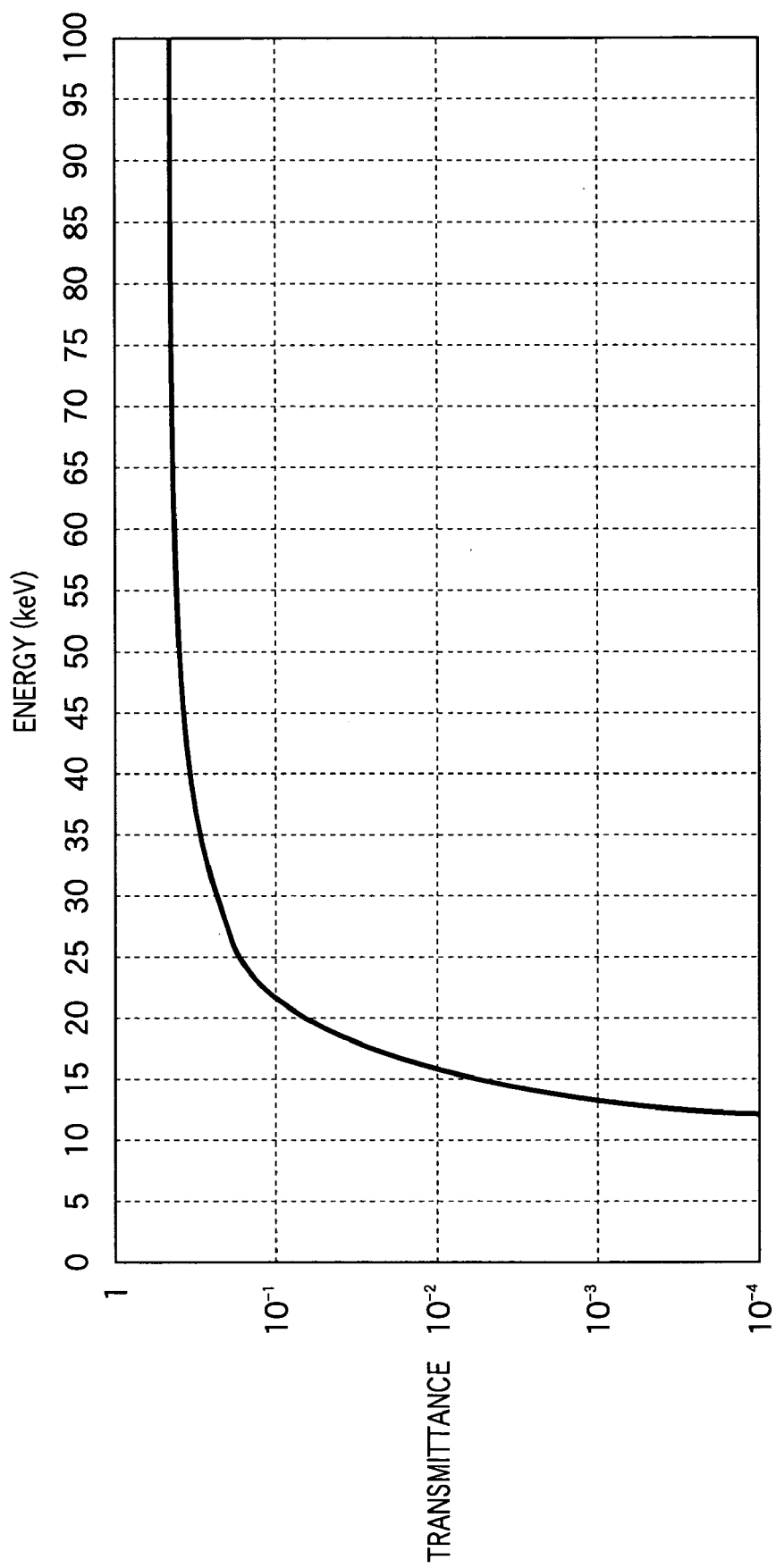
FIG. 3 is a graphical representation showing transmittance as a function of X-ray energy.

Next, as the object 10, a breast is assumed. FIG. 3 shows transmittance as a function of X-ray energy. Note that β is obtained by assuming standard fat composition and the thickness of the object 10 is assumed as d=5 cm. As shown in FIG. 3, the lower the energy, the more drastically the transmittance is reduced. On this account, the X-ray energy (E=3.3 keV, 1.7 KeV, and 5.0 keV) as described in T. E. Gureyev et al. "Quantitative In-Line Phase-Contrast Imaging with Multienergy X Rays", Physical Review Letter, Vol. 86, No. 25 (2001), pp. 5827-5830, is not suitable in the case where the object having a larger thickness such as a breast is subjected to imaging. Further, in order to improve energy efficiency with high transmittance, it is desired that the X-ray energy be on the order of 22 keV at which the transmittance is about 10%. However, in order to allow the X-ray to reach the sensor 103 while suppressing the amount of X-ray absorption (exposure amount) by the object 10, equal or more than 16 keV of X-ray energy at which the transmittance is at least equal or more than 1% is required.

On the other hand, the phase-contrast method is an imaging method of detecting a phase change by separating the object 10 and the sensor 103 in FIG. 2 at a predetermined distance. The phase change of the X-ray by the object 10 is expressed as $e^{-ik(1-\delta)d}$ in Eq. (8). Here, with reference to the $e^{-ikd}$ of the phase change of the X-ray in the case where the object is vacuum (δ=0), the phase change of the X-ray by the object 10 is expressed by $e^{ik\delta d}$. The phase is kδd on the shoulder of the exponential.

Figure 4:
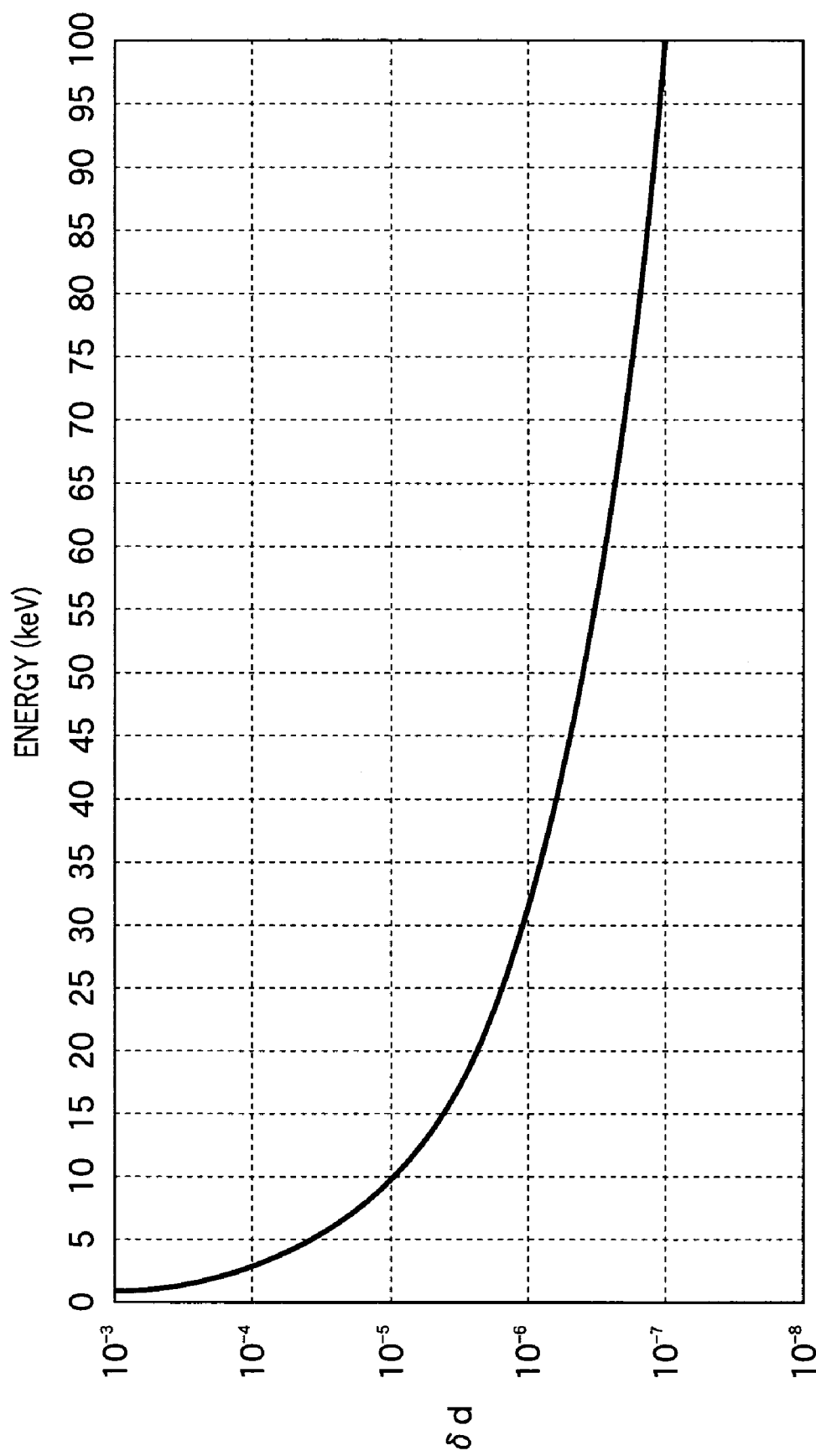
FIG. 4 is a graphical representation showing relationship between δd and energy.

Here, δ has dependence on X-ray energy. FIG. 4 shows the relationship between δd and energy in the case where the standard fat composition is assumed. Note that d=5 cm.

By the way, considering the TIE as a basis when phase estimation shown in FIG. 4 in one-dimension for simplicity, neglecting signs, and further arranging by substituting the phase φ=kδd, the TIE is expressed as the follows.

$$-\frac{1}{I}\frac{\partial I}{\partial z} \cong \frac{\partial^2 d\delta}{\partial x^2} \quad (12)$$

Here, the left side is a value representing how much the intensity I of the X-ray changes according to the distance z as a ratio relative to the intensity I, and the value obtained by experiments is at most 1% ($|(1/I)\times(\partial I/\partial z)| \geq 10^{-2}$). Further, the right side is a value dependent on how much the value of δd changes locally, and for the purpose of diagnosis, it is desirable that the phase change on the order of $10^{-6}$ radian of 10 μm (=$10^{-5}$ m) is detected. Therefore, the right side of Eq. (12) is expressed as follows.

$$\frac{\partial^2 d\delta}{\partial x^2} \cong \frac{10^{-6} d\delta}{(10^{-5})^2} \quad (13)$$

Furthermore, substituting $-(1/I)\times(\partial I/\partial Z) \geq 10^{-2}$ into the left side of Eq. (12) and arranging it, it is expressed as follows.

$$10^{-2} \leq \frac{10^{-6}}{10^{-10}} d\delta \quad (14)$$

$$d\delta \geq 10^{-6} \quad (15)$$

Referring to FIG. 4 again, $d\delta \geq 10^{-6}$ is held in the case where the X-ray energy is equal or less than about 30 keV. Thus, it is desired that the imaging is performed by using the X-ray having energy from 16 keV to 30 keV.

Figure 5:
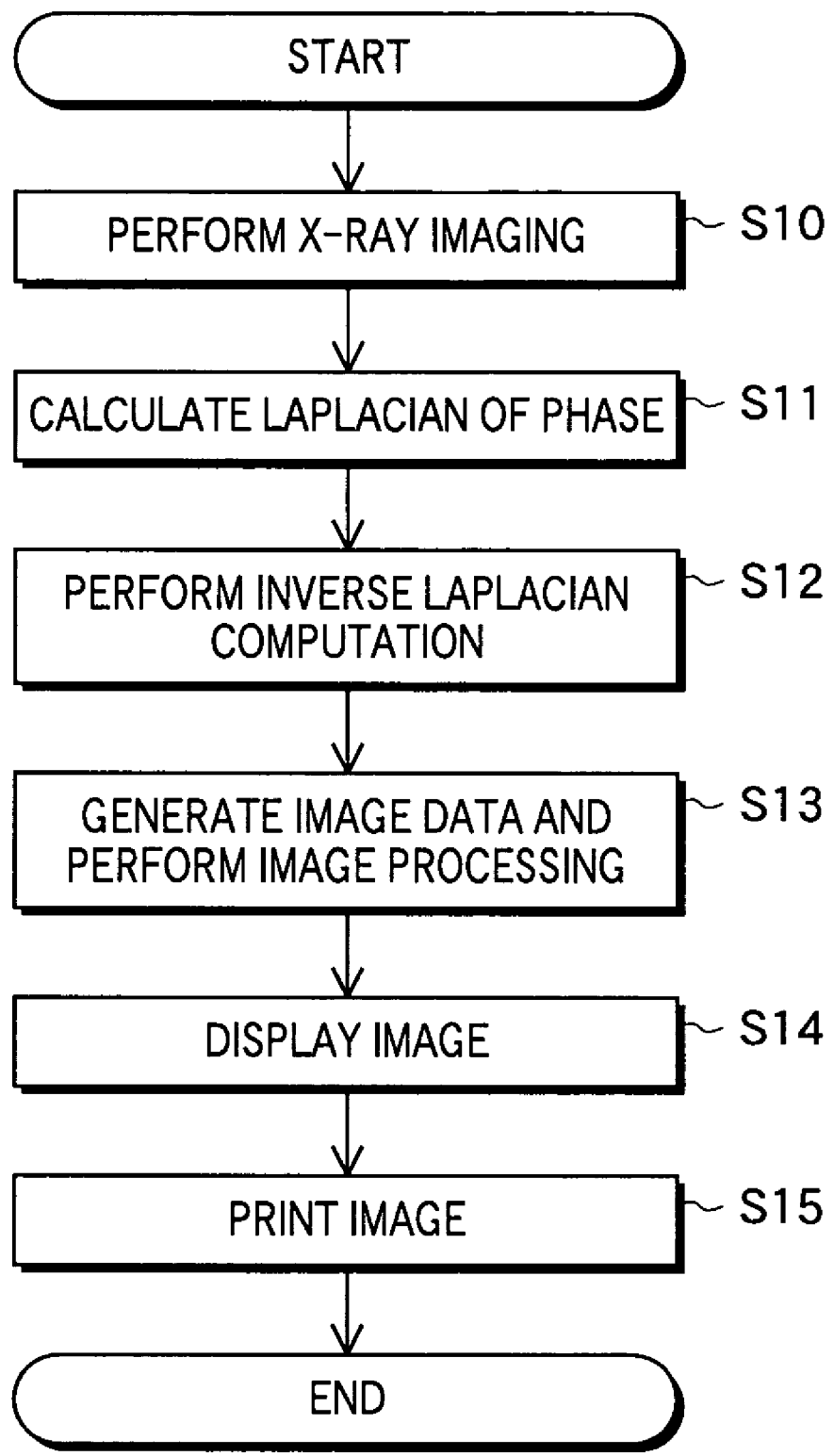
FIG. 5 is a flowchart showing a phase information restoring method according to the first embodiment of the present invention.
Figure 6:
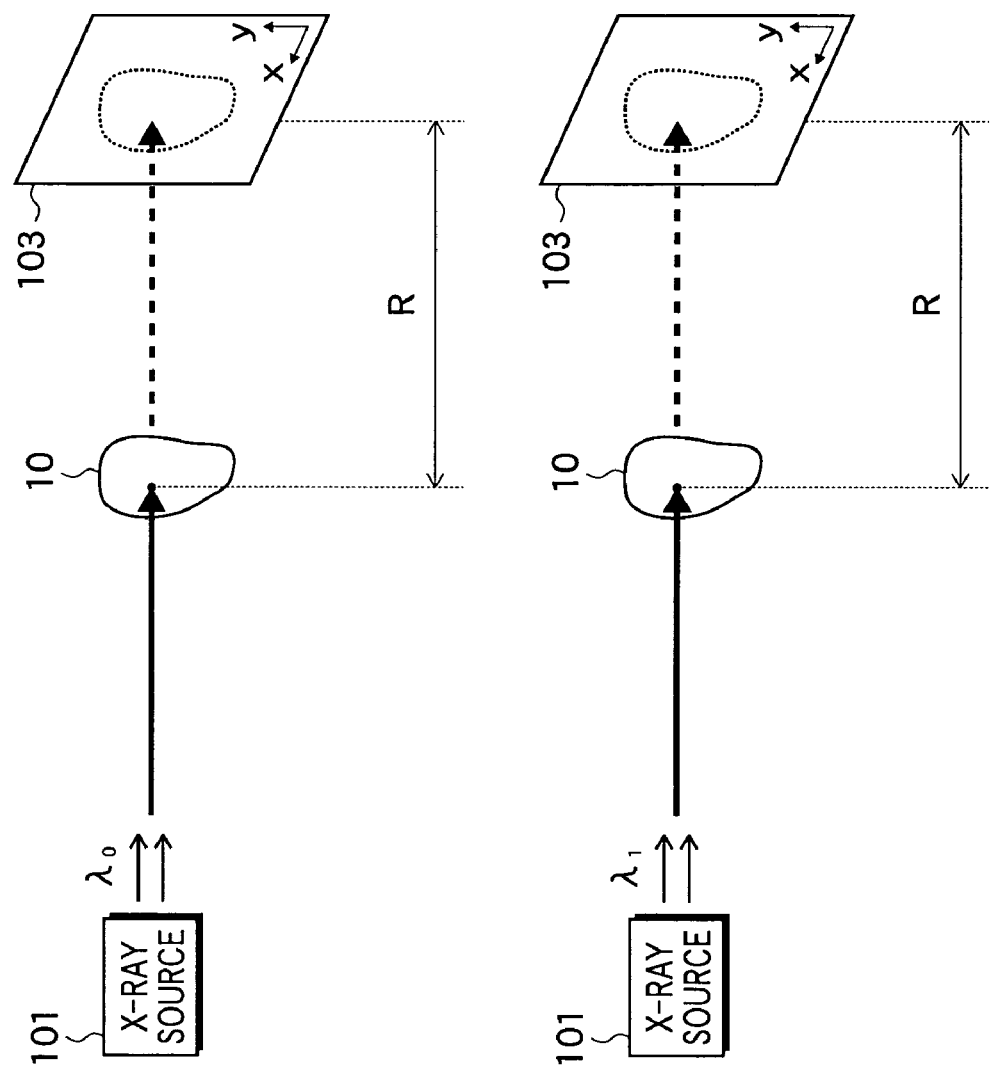
FIG. 6 is a diagram showing the imaging unit being generating each of two kinds of X-rays having different wavelengths $\lambda_0$ and $\lambda_1$ at the same imaging distance.

Next, referring to FIGS. 1, 5, and 6, a phase information restoring method according to the first embodiment of the present invention will be described. FIG. 5 is a flowchart showing the phase information restoring method according to the first embodiment of the present invention. In the embodiment, a visible image is constructed by using the phase-contrast method based on detection data representing two diffraction fringe images taken at the same imaging distance by using X-rays having different wavelengths $\lambda_0$ and $\lambda_1$. Note that the X-ray having the wavelength $\lambda_0$ or $\lambda_1$ represents a highly monochromatic X-ray with the wavelength $\lambda_0$ or $\lambda_1$ as a center wavelength, and may not strictly be an X-ray having single wavelength of $\lambda_0$ or $\lambda_1$. However, the center value of the energy of the X-ray having the wavelength $\lambda_0$ or $\lambda_1$ is assumed to satisfy the condition from 16 keV to 30 keV.

First, at step S10, X-ray imaging operation is performed. That is, as shown in FIG. 6, X-ray imaging is performed by positioning the sensor 103 in the position where the imaging distance is R and applying an X-ray having wavelength $\lambda_0$ to the object 10. Then, X-ray imaging is performed by applying an X-ray having wavelength $\lambda_1$ to the object 10. Thereby, the detection data representing diffraction fringe images are obtained.

By the X-ray imaging at step S10, detection data $I(r_\perp, R, \lambda_0)$ and $I(r_\perp, R, \lambda_1)$ are sequentially inputted to the image constructing unit 200. Here, the detection data $I(r_\perp, R, \lambda_0)$ represents intensity of the diffraction X-ray having the wavelength $\lambda_0$ in the position $r_\perp=(x, y)$ on a plane at the imaging distance of R. Similarly, the detection data $I(r_\perp, R, \lambda_1)$ represents intensity of diffraction X-ray having the wavelength $\lambda_1$ in the position $r_\perp=(x, y)$ on the plane at the imaging distance of R. These detection data are sequentially stored in the storage unit 201 of the image constructing unit 200.

Next, at steps S11 and S12, the image constructing unit 200 restores phase $\phi(r_\perp, 0, \lambda_0)$ of the X-ray just after transmitted through the object on the basis of the detection data $I(r_\perp, R, \lambda_0)$ and $I(r_\perp, R, \lambda_1)$ stored in the storage unit 201.

First, at step S11, the Laplacian processing unit 202 obtains a Laplacian $f(r_\perp, 0, \lambda_0) = \nabla^2 \phi(r_\perp, 0, \lambda_0)$ of the phase $\phi(r_\perp, 0, \lambda_0)$ by using the following equation (16).

$$f(r_\perp, 0, \lambda_0) = \nabla^2 \phi(r_\perp, 0, \lambda_0) \quad (16)$$

$$= -\frac{2\pi}{R\Delta\lambda}(\sigma g_0 - \sigma^{-2} g_1)$$

Where, $$g_0 = ln\{I(r_\perp, R, \lambda_0)\} \quad (17)$$

$$g_1 = ln\{I(r_\perp, R, \lambda_1)\} \quad (18)$$

$$\Delta\lambda = \lambda_1 - \lambda_0, \sigma = \lambda_1/\lambda_0$$

Accordingly, $g_0$ and $g_1$ are obtained by substituting the detection data $I(r_\perp, R, \lambda_0)$ and $I(r_\perp, R, \lambda_1)$ into Eqs. (17) and (18), respectively, and further, by substituting $g_0$ and $g_1$ into Eq. (16), the Laplacian $f(r_\perp, 0, \lambda_0)$ of the phase can be obtained.

Furthermore, at step S12, the inverse Laplacian processing unit 203 obtains the phase $\phi(r_\perp, 0, \lambda_0)$ by performing inverse Laplacian computation on the Laplacian $f(r_\perp, 0, \lambda_0)=\nabla^2 \phi(r_\perp, 0, \lambda_0)$ of the phase obtained at step S11.

Here, the inverse Laplacian computation will be described in detail. A Fourier transform on $f(r_\perp, 0, \lambda_0)$ is expressed by the following equation (19).

$$F[f(r_\perp, 0, \lambda_0)] = F[\nabla^2 \phi(r_\perp, 0, \lambda_0)] \qquad (19)$$
$$= -4\pi^2(u^2 + v^2)[\phi(r_\perp, 0, \lambda_0)]$$

Where, $F[\ ]$ represents a Fourier transform and u and v are spatial frequencies that correspond to x and y.

Hereby, the phase $\phi(r_\perp, 0, \lambda_0)$ is expressed as Eq. (20).

$$\phi(r_\perp, 0, \lambda_0) = F^{-1}\left[-\frac{1}{4\pi^2(u^2 + v^2)} F[f(r_\perp, 0, \lambda_0)]\right] \qquad (20)$$

Where, $F^{-1}[\ ]$ represents an inverse Fourier transform. Using Eq. (20), the inverse Laplacian computation can be performed. That is, the restored phase $\phi(r_\perp, 0, \lambda_0)$ can be obtained by performing the Fourier transform on $f(r_\perp, 0, \lambda_0)$, multiplying by $\{-4\pi^2(u^2+v^2)\}^{-1}$ and then performing the inverse Fourier transform thereon.

Here, a value of $\{-4\pi^2(u^2+v^2)\}^{-1}$ may be calculated in advance within the range where $|u|$ and $|v|$ are not larger than a predetermined value so that the calculated value can be used when the computation expressed by Eq. (20) is performed. That is, in the case where the predetermined value "const" is set, for $|u|, |v| \leq$ const, the value of the following expression is used in Eq. (20).

$$\{-4\pi^2(u^2+v^2)\}^{-1}=(\text{the value calculated in advance})$$

On the other hand, for $|u|, |v| >$ const, the value of the following expression is used in Eq. (20).

$$-4\pi^2(u^2+v^2)\}^{-1}=0$$

Thereby, the inverse Laplacian computation can be performed at high speed.

Next, at step S13, the image processing unit 204 generates image data on the basis of the restored phase $\phi(r_\perp, 0, \lambda_0)$. That is, the image processing unit 204 converts the phase $\phi(r_\perp, 0, \lambda_0)$ in each pixel into data representing brightness, and performs necessary image processing such as tone processing and interpolation processing.

Then, as far as necessary, at step S14, the display unit 300 displays a visible image on the basis of the image data on a display, and at step S15, the output unit 400 prints it out on a film, etc.

In the embodiment, an X-ray is used when performing imaging on an object. However, not limited to the X-ray but any radiation that can form diffraction images by being transmitted through the object and satisfies the energy condition from 16 keV to 30 keV can be used. For example, corpuscular beams, etc. including an electron ray can be cited. Further, in the embodiment, phase is restored by using two X-rays having different energy, however, as described in T. E. Gureyev et al. "Quantitative In-Line Phase-Contrast Imaging with Multienergy X Rays", the phase may be restored by using three X-rays having different energy.

Furthermore, in the embodiment, a synchrotron radiation source is used when imaging is performed on an object, a radiation source generating beams other than synchrotron radiation may be used. For example, the electron-storage-type high-brightness hard X-ray generator, which has been developed in the Ritsumeikan University, can generate X-ray having as high brightness and directionality as synchrotron radiation despite of its desktop size. X-ray generated by this generator has coherence, and even though the X-ray has plural wavelengths, they can be monochromatized by combining with monochromatizing crystal. Moreover, the ray source developed by The Femtosecond Technology Research Association (FESTA) generates ultra short pulse high-brightness X-ray on the basis of a principle of backward Compton scatter. This ray source is compact and portable, and can generate X-ray having not only coherence but also high directionality and monochromaticity. Note that, in the case where a point radiation source is used as the radiation source, it is desirable to perform correction on the detection data obtained by X-ray imaging in view of an enlargement ratio before performing data processing in the image constructing unit.

Next, a modified example of the phase information restoring apparatus according to the first embodiment of the present invention will be described by referring to FIG. 7. The phase information restoring apparatus shown in FIG. 7 has an imaging unit 110 and a reading unit 500. Other constitution is the same as that of the phase information restoring apparatus shown in FIG. 1.

In the imaging unit 110, as a screen used for recording image information, a photo stimulable phosphor sheet (recording sheet) is used instead of the sensor 103 in the imaging unit 100 shown in FIG. 2.

The photo stimulable phosphor (storage phosphor) is a material that, when applied with radiation, a part of the radiation energy is stored therein, and when applied with excitation light such as visible light afterward, stimulated fluorescence is generated depending on the stored energy. When a radiation image of an object such as a human body, etc. is taken and recorded on the sheet that is applied with the photo stimulable phosphor, and scanned by the excitation light such as laser light, stimulated fluorescent light is generated. Therefore, detection data can be obtained by reading the light photoelectrically. After the detection data is appropriately processed, the radiation image can be displayed as a visible image by being outputted to a display such as a CRT or printed out on a film by a laser printer, etc.

Figure 7:
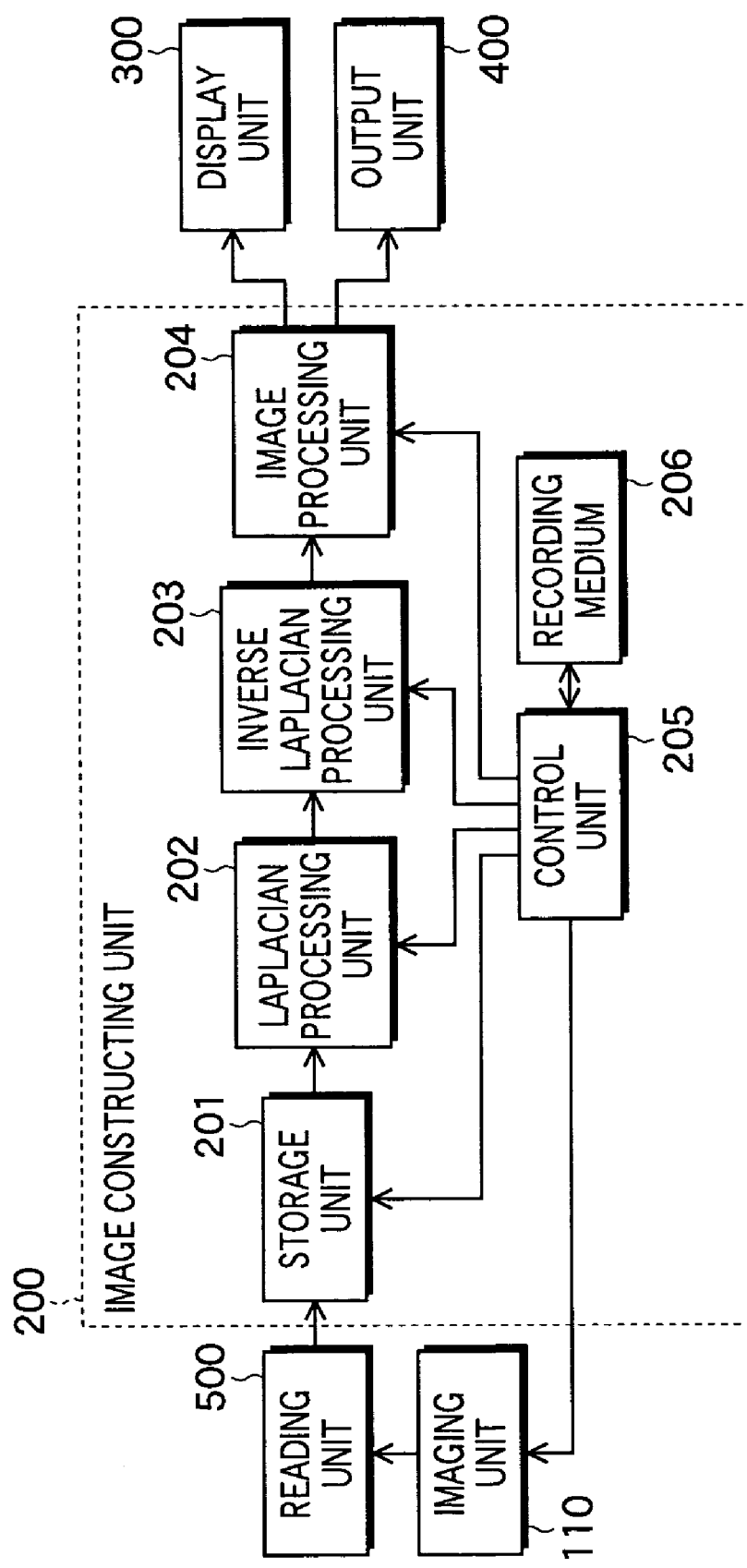
FIG. 7 is a block diagram showing a modified example of the phase information restoring apparatus according to the first embodiment of the present invention.
Figure 8:
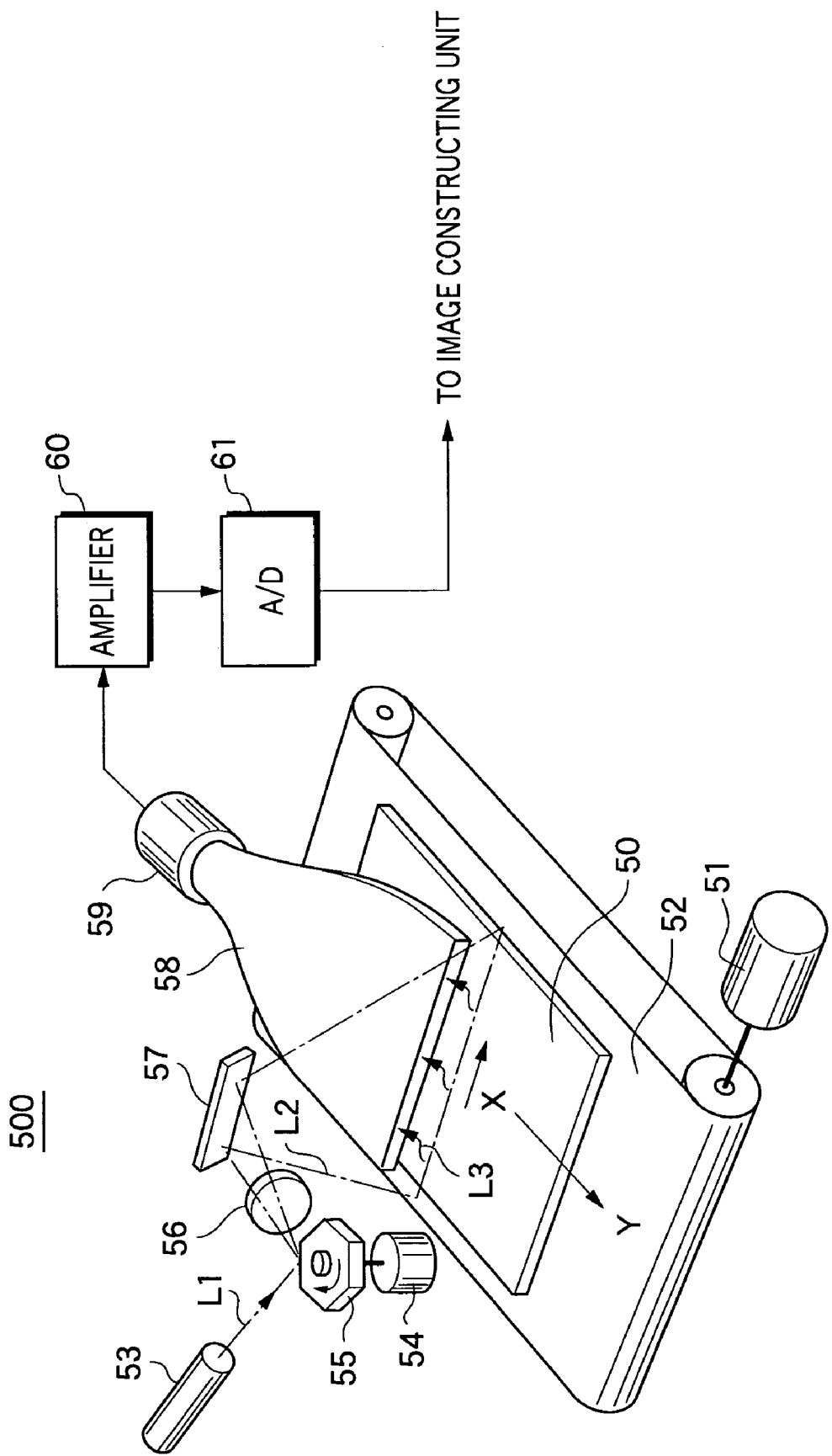
FIG. 8 is a diagram showing a constitution of a reading unit shown in FIG. 7.

The reading unit 500 shown in FIG. 7 is used for reading the radiation image recorded on the recording sheet. Here, referring to FIG. 8, constitution and operation of the reading unit 500 will be described. The recording sheet 50 on which image information has been recorded is set in a predetermined position of the reading unit 500. The recording sheet 50 is carried in a direction of a Y axis by a sheet carrying means 52 driven by a motor 51. On the other hand, a beam L1 emitted from the laser source 53 is reflected and deflected by a rotating multifaceted mirror 55 that is driven by a motor 54 and rotating at high speed in a direction of an arrow, and passes through a convergent lens 56. Then, the beam L1 has its optical path changed by the mirror 57 and scans the recording sheet 50 in a direction of an X axis. By this scanning, excitation light L2 is applied to the recording sheet 50, and stimulated fluorescent light L3 having quantity depending to the stored and recorded radiation image information is emitted from the applied part. The stimulated fluorescent light L3 is guided by an optical guide 58 and photoelectrically detected by a photomultiplier 59. An analogue signal outputted from the photomultiplier 59 is amplified by an amplifier 60 and digitized by an A/D converter 61. The detection data outputted from the A/D converter 61 is inputted to the image constructing unit 200.

Image information representing plural interference fringe images obtained in different energy of X-rays can be obtained by performing radiation imaging while changing the energy of the emitted X-rays and using plural recording sheets in the imaging unit 110, and reading image information from the respective recording sheets in the reading unit 500. The image constructing unit 200 performs phase restoration on the basis of the detection data and generates image data. The processing in the image constructing unit 200 is the same as that described by referring to FIG. 5.

Figure 9:
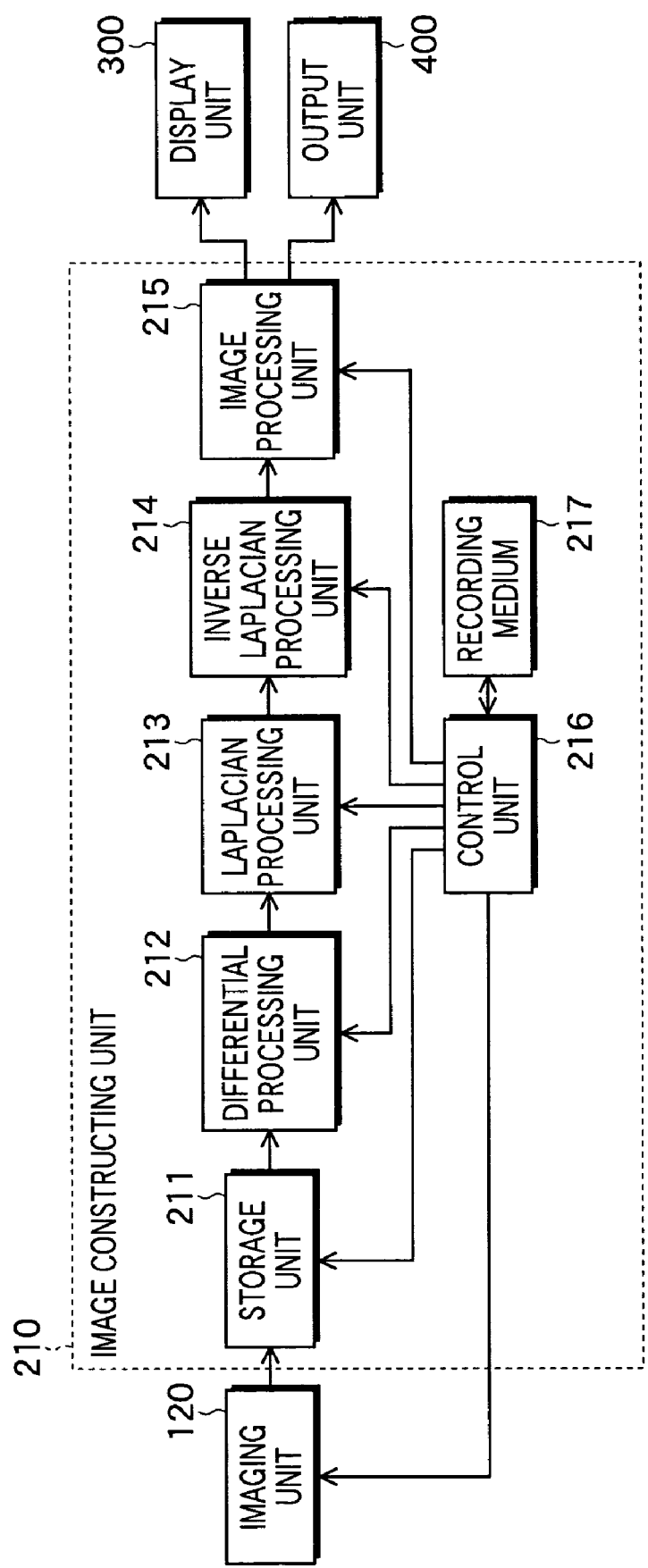
FIG. 9 is a block diagram showing a constitution of a phase information restoring apparatus according to a second embodiment of the present invention.

Next, a phase information restoring apparatus according to a second embodiment of the present invention will be described. FIG. 9 is a block diagram showing a constitution of the phase information restoring apparatus according to the second embodiment of the present invention.

As shown in FIG. 9, this phase information restoring apparatus has an imaging unit 120 for outputting detection data that represents radiation image information on an object by applying X-rays to the object, an image constructing unit 210 for generating image data by restoring phase information on the basis of the detection data. Other constitution is the same as that in FIG. 1.

Figure 10:
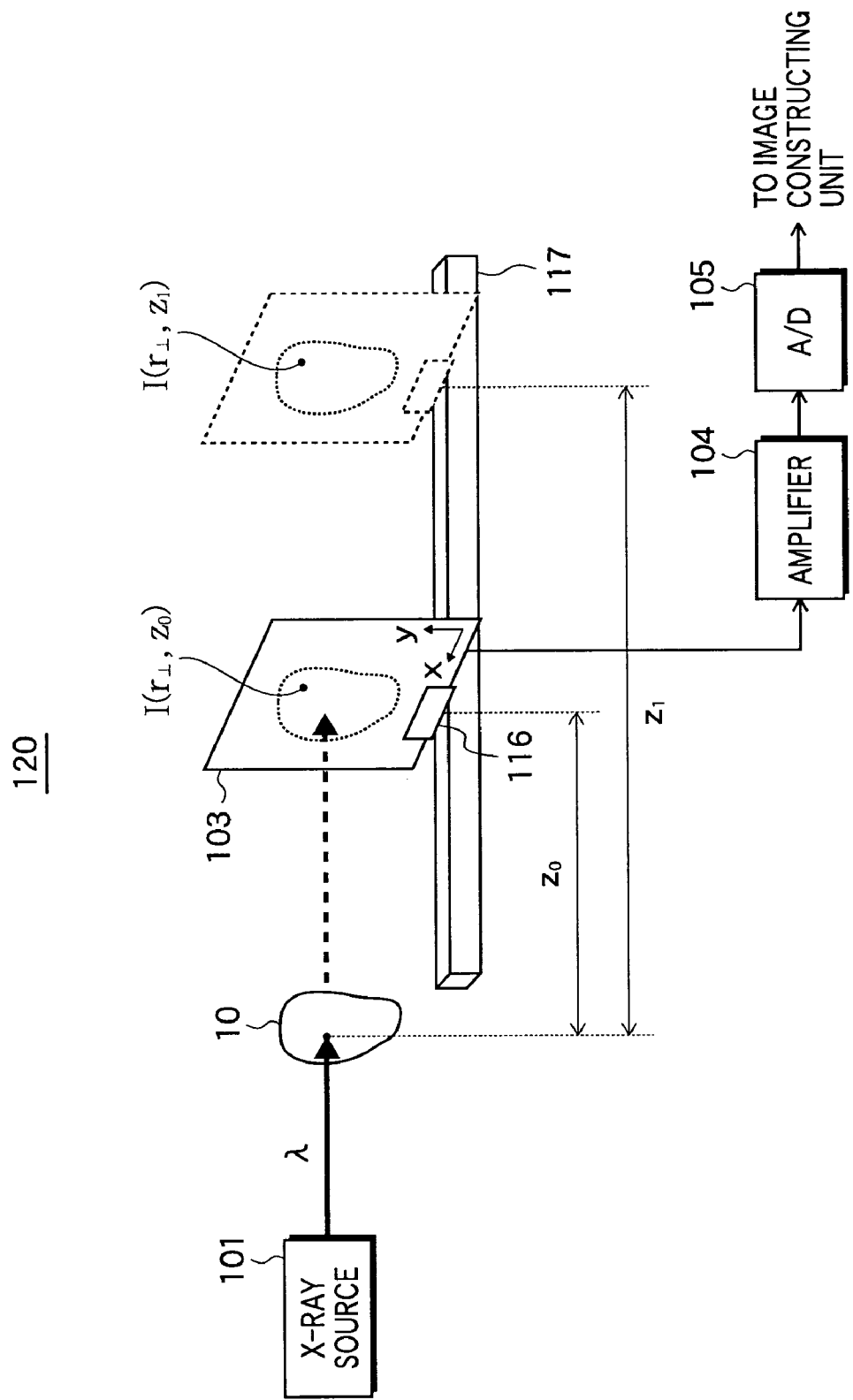
FIG. 10 is a diagram showing a constitution of the imaging unit shown in FIG. 9.

FIG. 10 is a diagram showing a constitution of the imaging unit 120. The imaging unit 120 includes a radiation source 101 and a sensor 103. The X-ray generated from the radiation source 101 is transmitted through the object 10 and enters a sensor 103 to generate diffraction fringes.

The sensor 103 is held by a holding portion 116. The holding portion 116 is movably supported on a rail 117. The position of the holding portion 116 is controlled by a control unit, which will be described later, of the image constructing unit 210, and a distance between the object 10 and the sensor 103 is changed under the control of the control unit.

Further, the imaging unit 120 includes an amplifier 104 and an A/D converter 105. The amplifier 104 amplifies detection signal outputted from the sensor 103. The A/D converter 105 converts the detection signal amplified by the amplifier 104 into a digital signal (referred to as "image signal" or "detection data"), and outputs the detection data to the image constructing unit 210.

Referring to FIG. 9 again, the image constructing unit 210 has a storage unit 211 for temporarily storing the detection data outputted from the imaging unit 120, a differential processing unit 212 for obtaining a differential coefficient between detection data at different imaging distances, a Laplacian processing unit 213 for calculating a value that corresponds to a Laplacian of phase, an inverse Laplacian processing unit 214 for performing inverse Laplacian computation for performing phase restoration, an image processing unit 215 for generating image data on the basis of the phase information in a position of the sensor outputted from the inverse Laplacian processing unit 214, and a control unit 216 for controlling the respective units 211-215 and the imaging distance in the imaging unit 120. The image constructing unit 210 maybe configured with a digital circuit or software and a CPU. With a CPU, the control unit 216 including the CPU processes the detection data on the basis of a phase information restoring program recorded on a recording medium 217. As the recording medium 217, a flexible disk, a hard disk, an MO, an MT, a RAM, a CD-ROM, a DVD-ROM, etc. are applicable.

Figure 11:
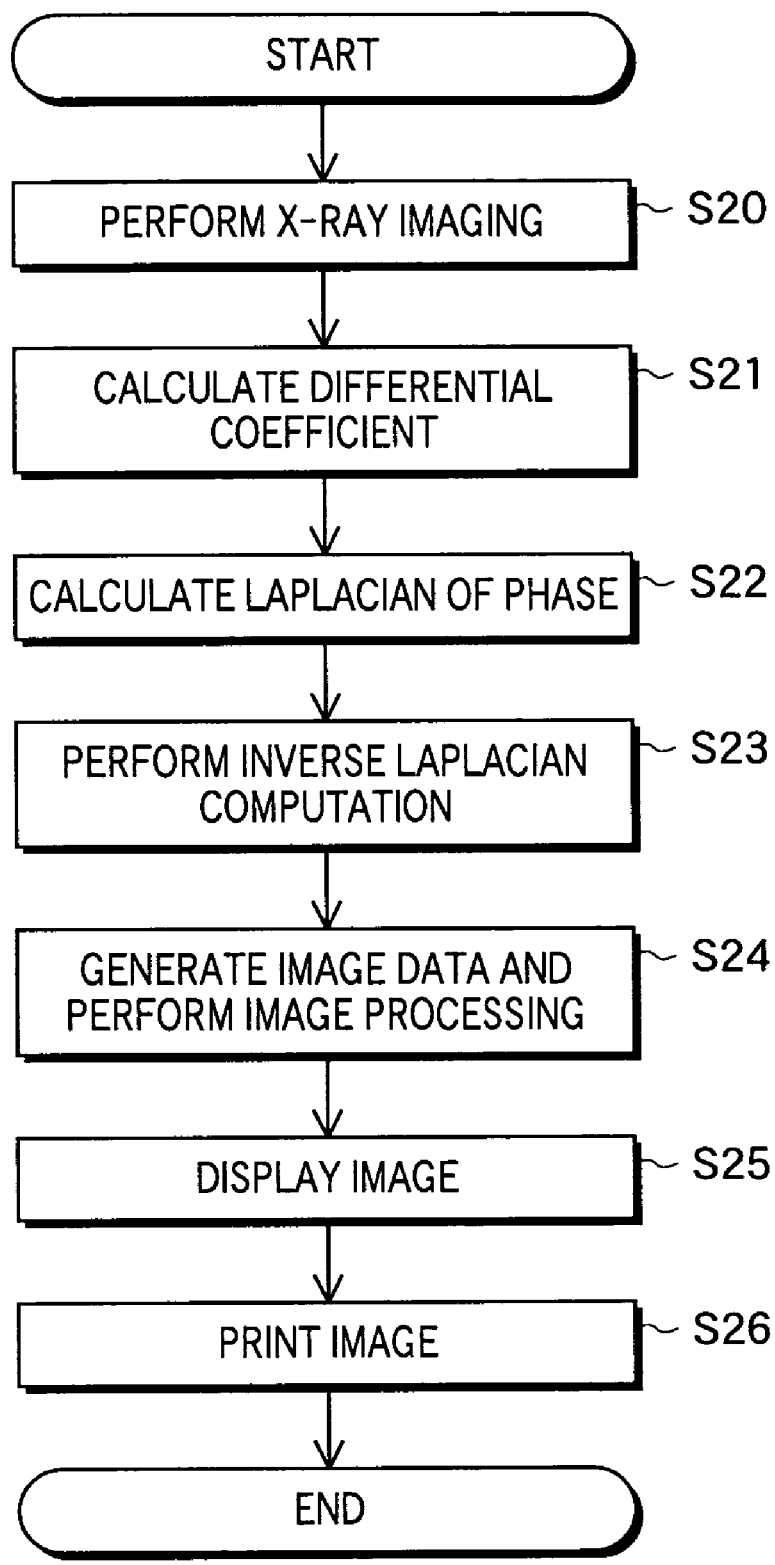
FIG. 11 is a flowchart showing a phase information restoring method according to the second embodiment of the present invention.

Next, a phase information restoring method according to the second embodiment of the present invention will be described by referring to FIGS. 9-11. FIG. 11 is a flowchart showing the phase information restoring method according to the second embodiment of the present invention. In the embodiment, a visible image is produced by using image information that represents two diffraction fringe images taken at different imaging distances $z_0$ and $z_1$ by using X-rays having the same wavelength $\lambda$. Note that the X-ray having the wavelength $\lambda$ indicates a highly monochromatic X-ray with the wavelength $\lambda$ as a center wavelength, and may not strictly be an X-ray having single wavelength of $\lambda$. Note that the center value of the energy of the X-ray having the wavelength $\lambda$ satisfies the condition from 16 keV to 30 keV.

First, at step S20, the wavelength of the X-ray of the X-ray source is set to $\lambda$, and X-ray imaging is performed while changing the position of the sensor 103. That is, the X-ray imaging is performed by first positioning the sensor 103 in the position where the imaging distance is $z_0$ and applying an X-ray to the object 10 as shown in FIG. 10. Then, the X-ray imaging is similarly performed after moving the sensor 103 to the position where the imaging distance is $z_1$. Thereby, the image information representing diffraction fringe images are obtained.

By the X-ray imaging at step S20, detection data $I(r_\perp, z_0, \lambda)$ and $I(r_\perp, z_1, \lambda)$ are sequentially inputted to the image constructing unit 210. Here, the detection data $I(r_\perp, z_0, \lambda)$ represents intensity of the diffraction X-ray in the position $r_\perp = (x, y)$ on a plane at the imaging distance of $z_0$. Similarly, the detection data $I(r_\perp, z_1, \lambda)$ represents intensity of diffraction X-ray in the position $r_\perp = (x, y)$ on a plane at the imaging distance of $z_1$. These detection data are sequentially stored in the storage unit 211 of the image constructing unit 210.

Next, at steps S21 to S23, the image constructing unit 210 restores phase in the position of the sensor on the basis of the detection data stored in the storage unit 211.

First, at step S21, the differential processing unit 212 obtains a differential coefficient between detection data $I(r_\perp, z_1, \lambda)$ and detection data $I(r_\perp, z_0, \lambda)$ by using the following equation (21).

$$\frac{\partial I(r_\perp, z_0, \lambda)}{\partial z} = \frac{I(r_\perp, z_1, \lambda) - I(r_\perp, z_0, \lambda)}{z_1 - z_0} \tag{21}$$

Then, at step S22, the Laplacian processing unit 213 obtains a Laplacian $f(r_\perp, z, \lambda) = \nabla^2 \phi(r_\perp, z, \lambda)$ of the phase on the basis of the differential coefficient obtained at step S21 and the detection data stored in the storage unit 201 by using the following equation (22).

$$f(r_\perp, z, \lambda) = -\frac{\kappa}{I(r_\perp, z_0, \lambda)} \frac{\partial I(r_\perp, z_0, \lambda)}{\partial z} \tag{22}$$

In Eq. (22), the differential coefficient is divided by the detection data $I(r_\perp, z_0, \lambda)$ at the shorter imaging distance. However, it may be divided by the detection data $I(r_\perp, z_1, \lambda)$ at the longer imaging distance. Further, it may be divided by the detection data subjected to LPF (low pass filter) processing.

Furthermore, at step S23, the inverse Laplacian processing unit 214 obtains the phase $\phi(r_\perp, z, \lambda)$ by performing inverse Laplacian computation on the Laplacian $f(r_\perp, z, \lambda) = \nabla^2 \phi(r_\perp, z, \lambda)$ of the phase obtained at step S22. That is, the following equation (23) that represents the phase $\phi(r_\perp, z, \lambda)$ is obtained by performing Fourier transform on the Laplacian $f(r_\perp, z, \lambda)$ of the phase and transforming it.

$$\phi(r_\perp, z, \lambda) = F^{-1}\left[-\frac{1}{4\pi^2(u^2+v^2)}F[f(r_\perp, z, \lambda)]\right] \quad (23)$$

By using Eq. (23), the inverse Laplacian computation can be performed. By the way, the detailed method of inverse Laplacian computation is the same as that described in the first embodiment of the present invention.

Next, at step S24, the image processing unit 215 generates image data on the basis of the restored phase $\phi(r_\perp, z, \lambda)$ That is, the image processing unit 215 converts the phase $\phi(r_\perp, z, \lambda)$ in each pixel into data representing brightness, and performs necessary image processing such as tone processing and interpolation processing.

Then, as far as necessary, at step S25, the display unit 300 displays a visible image on the basis of the image data on a display, and at step S26, the output unit 400 prints it out on a film, etc.

Figure 12:
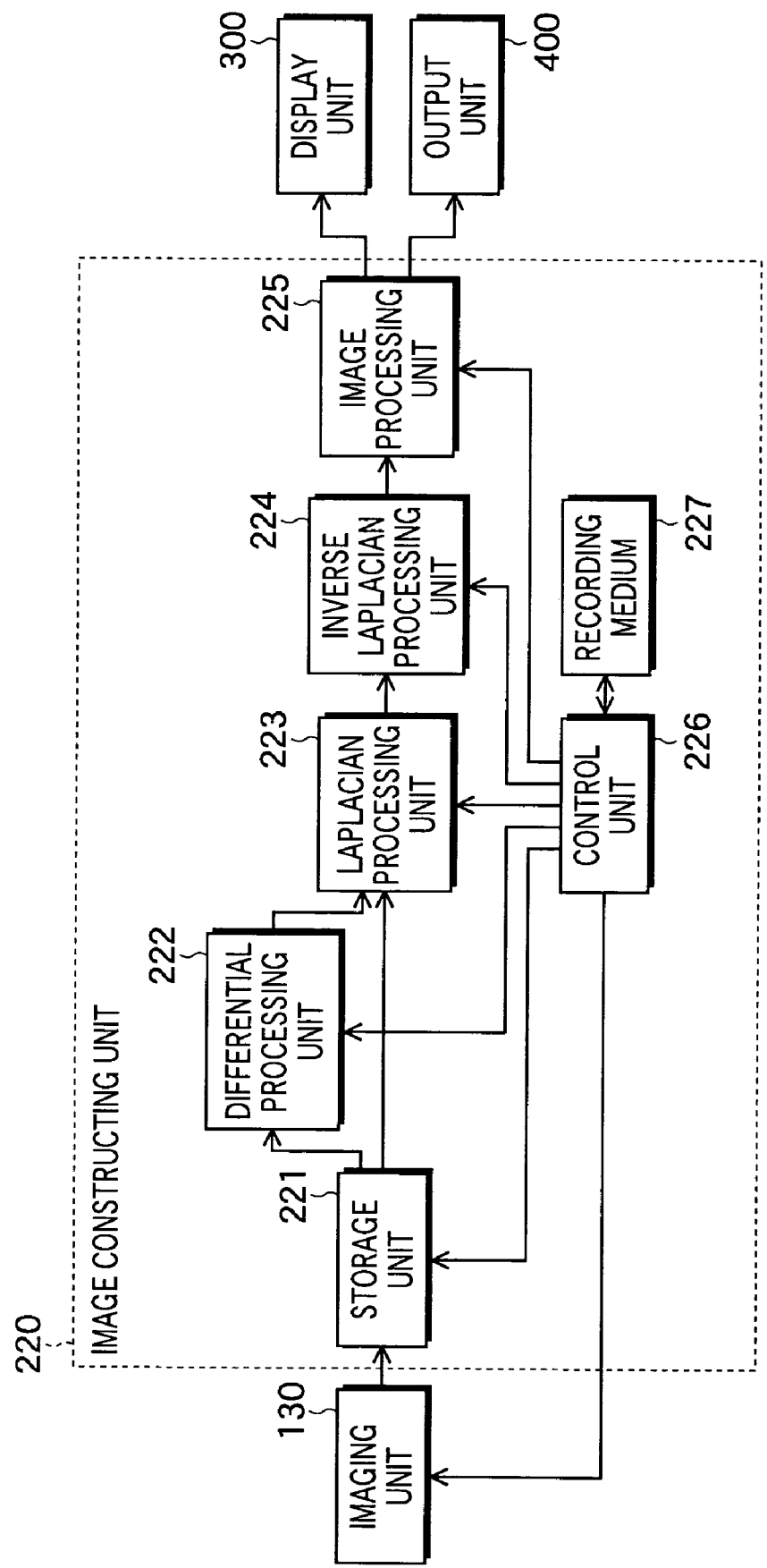
FIG. 12 is a block diagram showing a constitution of a phase information restoring apparatus according to a third embodiment of the present invention.

Next, a phase information restoring apparatus according to a third embodiment of the present invention will be described. FIG. 12 is a block diagram showing a constitution of the phase information restoring apparatus according to the third embodiment of the present invention. This phase information restoring apparatus has an imaging unit 130 and an image constructing unit 220. Other constitution is the same as that of the phase information restoring apparatus shown in FIG. 1.

Figure 13:
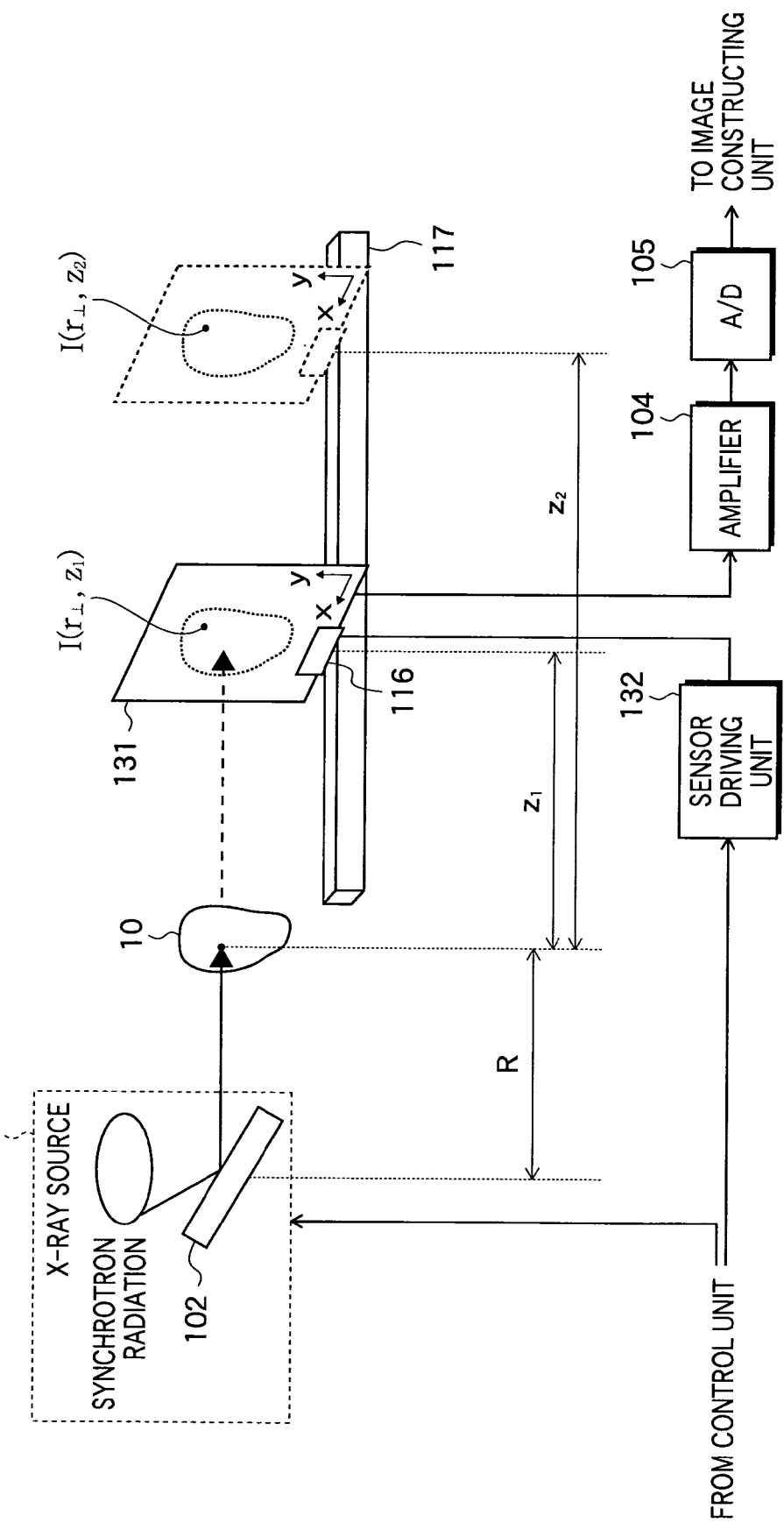
FIG. 13 is a diagram showing a constitution of an imaging unit shown in FIG. 12.

FIG. 13 is a diagram showing a constitution of the imaging unit 130. The imaging unit 130 includes a sensor 131. The sensor 131 is used as a screen for detecting the incident X-ray which produces diffraction fringes, and outputs detection signals representing intensity of diffracted X-ray entering the respective positions of the sensor 131. As the sensor 131, a two-dimensional sensor such as a CCD (charge coupled device) is used, which has a plurality of detecting elements that convert intensity of the incident X-ray into electric signals and output the signals.

Further, the imaging unit 130 also includes a sensor driving unit 132. The sensor driving unit 132 changes the distance between the object 10 and the sensor 131 by driving a holding portion 116 under control of a control unit 226 of the image constructing unit 220, which will be described later. Other constitution of the imaging unit 130 is the same as that of the imaging unit shown in FIG. 10.

Referring to FIG. 12 again, the image constructing unit 220 has a storage unit 221 for temporarily storing the detection data outputted from the imaging unit 130, a differential processing unit 222 for obtaining a differential coefficient between detection data at different imaging distances, a Laplacian processing unit 223 for calculating a value that corresponds to a Laplacian of phase, an inverse Laplacian processing unit 224 for performing inverse Laplacian computation for performing phase restoration, an image processing unit 225 for generating image data on the basis of the restored phase information, and a control unit 226 for controlling the respective units 221-225 and the imaging distance in the imaging unit 130. The image constructing unit 220 may be configured with a digital circuit or software and a CPU. In the latter case, the control unit 226 including the CPU processes the detection data on the basis of a phase information restoring program recorded on a recording medium 227. As the recording medium 227, a flexible disk, a hard disk, an MO, an MT, a RAM, a CD-ROM, a DVD-ROM, etc. are applicable.

Figure 14:
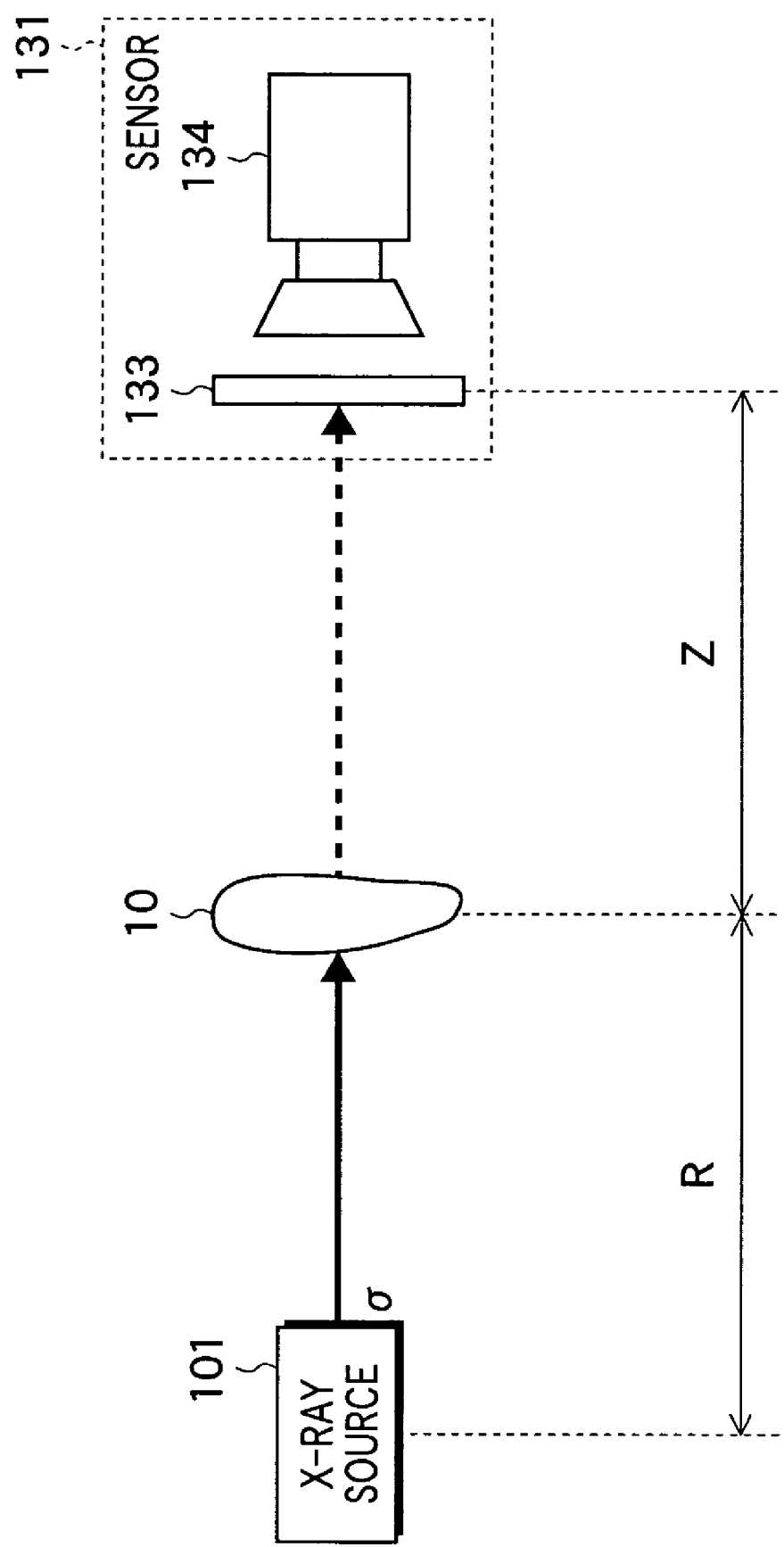
FIG. 14 is a diagram for explanation of a detection signal obtained by detecting an X-ray generated from an X-ray source having a finite focus size by using detecting elements included in a sensor.

Next, referring to FIG. 14, detection signals detected in a phase information restoring method according to the embodiment will be described. As shown in FIG. 14, in the embodiment, a combination of a fluorescent screen 133 and a CCD camera 134 is used as the sensor 131. That is, the fluorescence that is generated by applying the X-ray to the fluorescent screen 133 is taken by using the CCD camera 134 that is disposed oppositely to the X-ray source 101 relative to the fluorescent screen 133, thereby an X-ray is detected. In the embodiment, the X-ray source 101 having a finite focal spot size is used, and the CCD camera 134 with pixels in which longitudinal and lateral sizes of the pixels are $\Delta_X$ and $\Delta_Y$, respectively.

Here, a blur is produced in the image obtained by the X-ray generated from the X-ray source 101 having the finite focal spot size σ. Assuming that the distance between the object 10 and the X-ray source 101 is R, the imaging distance between the object 10 and the sensor 131 is z, and the focal spot sizes of the X-ray source in directions of an x axis and an y axis are $\sigma_X$ and $\sigma_Y$, respectively, blur function f(u, v) representing the blur of the image assumes normal distribution expressed by the following equation.

$$f(u, v) = \exp\left[-\frac{1}{2}a_X^2 u^2 - \frac{1}{2}a_Y^2 v^2\right] \quad (24)$$

Where, u and v are spatial frequency components in the directions of the x axis and the y axis in the sensor 131, respectively, and $a_X = 2\pi\sigma_X z/R$, $a_Y = 2\pi\sigma_Y z/R$.

Figure 15:
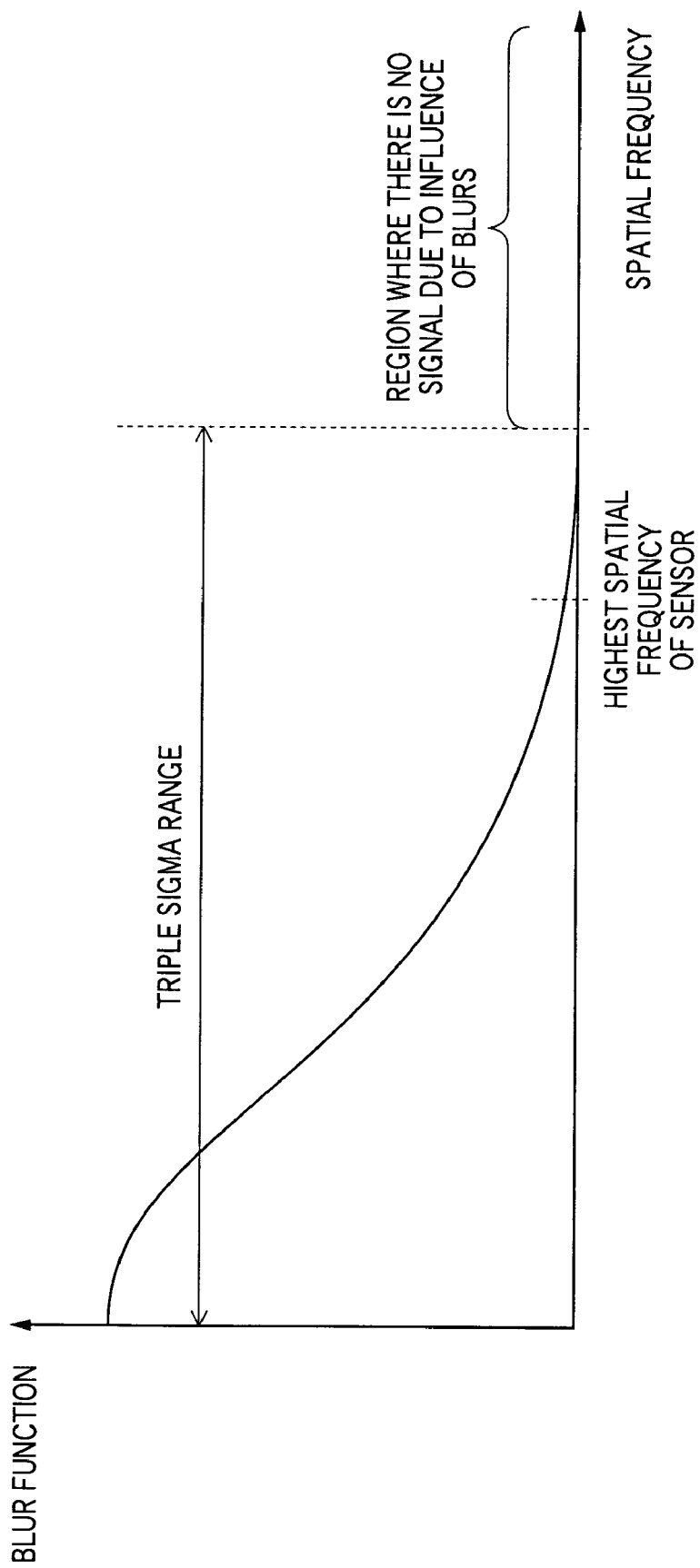
FIG. 15 is a graphical representation showing a blur function as a function of spatial frequency.

FIG. 15 shows the blur function as a function of spatial frequency. As shown in FIG. 15, the value of the blur function in the high spatial frequency region takes approximately zero. Therefore, even if the pixel size of the detecting elements that constitute the sensor is made smaller in order to obtain high-definition images, the detection signals of the images become few under the influence of blurs in the high spatial frequency region, thereby only noise is detected.

On this account, in order to reduce the influence of noise, the highest spatial frequency that the sensor can detect may be made lower than the spatial frequency at which the detection signals become few due to blurs. That is, assuming that the standard deviation in the blur function is sigma (σ), the highest spatial frequency that the sensor can detect maybe within the range of 3 sigma including 99% of the detection signals.

From Eq. (24), the triple sigma (3σ) range is represented by $u \leq 3/a_X$, $v \leq 3/a_Y$, and the highest spatial frequency relative to the pixel sizes $\Delta_X$, $\Delta_Y$ of the sensor is represented by $1/(2\Delta_X)$, $1/(2\Delta_Y)$ according to the sampling theorem. Therefore, it is understood that the pixel sizes $\Delta_X$, $\Delta_Y$ may satisfy the following equation in order to reduce the influence of noise.

$$\frac{1}{2\Delta_X} \leq \frac{3}{a_X}, \frac{1}{2\Delta_Y} \leq \frac{3}{a_Y} \quad (25)$$

By arranging the Eq. (25), the following equation (26) that shows the condition of the pixel sizes required for reducing the influence of noise can be obtained.

$$\Delta_X \geq a_X/6, \Delta_Y \geq a_Y/6 \quad (26)$$

For example, in the case where z=1.0 m, R=5.0 m, $\sigma_X=\sigma_Y=40$ μm, the pixel sizes may be equal or more than 8.4 μm.

Figure 16:
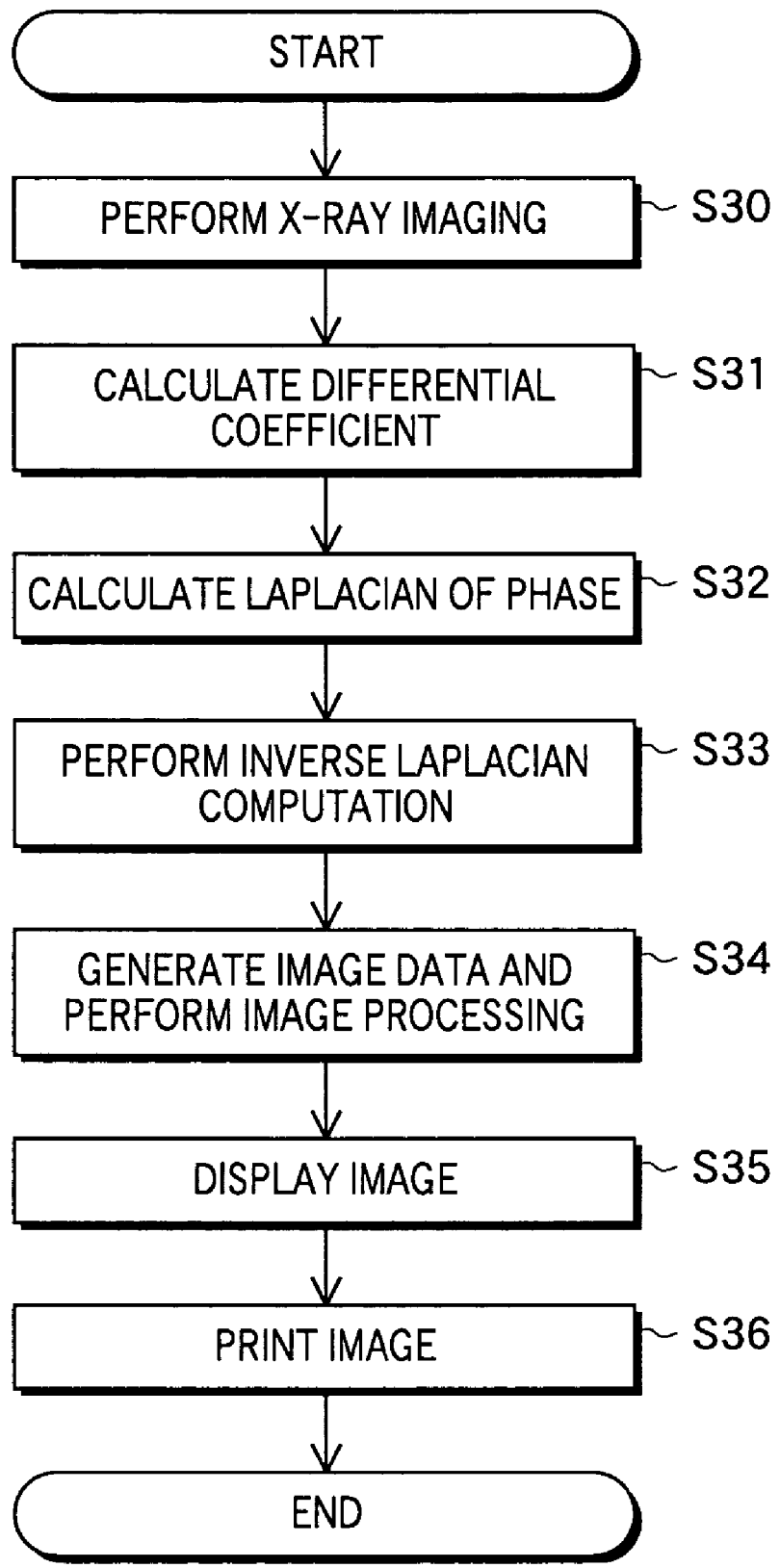
FIG. 16 is a flowchart showing a phase information restoring method according to the third embodiment of the present invention.

Next, referring to FIGS. 12, 13, and 16, the phase information restoring method according to the third embodiment of the present invention will be described. FIG. 16 is a flowchart showing the phase information restoring method according to the third embodiment of the present invention. In the embodiment, diffraction images are taken twice while changing the imaging distance, and a visible image is constructed on the basis of the detection data representing image information on these diffraction images by using the phase-contrast method.

First, at step S30, X-ray imaging operation is performed. That is, as shown in FIG. 13, the object is positioned in a position where the distance from the X-ray source 101 is R, and the sensor driving unit 132 positions the sensor 131 in a position where the imaging distance is $z_1$ under the control of the control unit 226, and an X-ray is applied to the object 10, thereby X-ray imaging is performed. Similarly, the X-ray imaging is performed by positioning the sensor 131 in a position where the imaging distance is $z_2$.

Here, assuming that the focal spot sizes of the X-ray source in directions of X, Y are $\sigma_X$, $\sigma_Y$, both the longitudinal and lateral pixel sizes of the detecting element of the sensor 131 are Δ, the larger one of the focal spot sizes $\sigma_X$, $\sigma_Y$ is σ, and the longer one of the imaging distances is z, the sensor driving unit 132 positions the sensor 131 using the detecting element having the pixel size that satisfies $\Delta \geqq \pi\sigma z/3R$ so that Eq. (26) may be satisfied.

By the X-ray imaging at step S30, the detection data I(x, y, $z_1$) and I(x, y, $Z_2$) that represent intensity of diffraction X-ray entering the pixel (x, y) on planes at the imaging distance of $z_1$ and $z_2$, respectively, are sequentially inputted to the image constructing unit 220, and stored in the storage unit 221. These detection data represent diffraction fringe image information on the planes at the respective imaging distances.

Next, at steps S31-S33, the image constructing unit 220 restores phase φ(x, y) in the position of the sensor on the basis of the detection data I(x, y, $z_1$) and I(x, y, $z_2$) stored in the storage unit 221.

First, at step S31, the differential processing unit 222 obtains a differential coefficient between the detection data I(x, y, $z_1$) and the detection data I(x, y, $Z_2$) using the following equation (27).

$$\frac{\partial I(x, y, z)}{\partial z} = \frac{I(x, y, z_2) - I(x, y, z_1)}{z_2 - z_1} \quad (27)$$

Then, at step S32, the Laplacian processing unit 223 obtains Laplacian f(x, y, z)=$\nabla^2$φ(x, y, z) of phase on the basis of the differential coefficient obtained at step S31 and the detection data stored in the storage unit 221 using the following equation (28).

$$f(x, y, z) = -\frac{\kappa}{I(x, y, z_1)} \frac{\partial I(x, y, z)}{\partial z} \quad (28)$$

Here, in Eq. (28), although the differential coefficient is divided by the detection data I(x, y, $z_1$) at a shorter imaging distance, it may be divided by the detection data I(x, y, $z_2$) at a longer imaging distance.

Further, at step S33, the inverse Laplacian processing unit 224 obtains phase φ(x, y, z) by performing inverse Laplacian computation on the Laplacian f(x, y, z)=$\nabla^2$φ(x, y, z) of the phase obtained at step S32. Note that the method of the inverse Laplacian computation is the same as that described in the first embodiment of the present invention.

Next, at step S34, the image processing unit 225 generates image data on the basis of the phase φ(x, y, z). That is, the image processing unit 225 converts the phase φ(x, y, z) in each pixel into data representing brightness and performs necessary image processing such as tone processing and interpolation processing.

Then, as far as necessary, at step S35, the display unit 300 displays a visible image on the basis of the image data on a display, and at step S36, the output unit 400 prints it out on a film, etc.

In the embodiment, an X-ray is used when performing imaging on an object. However, not limited to the X-ray but any radiation that can form diffraction images by being transmitted through the object, for example, corpuscular beams, etc. including an electron ray can be used. Alternatively, similarly to that described in the first embodiment of the present invention, a radiation source generating beams other than synchrotron radiation maybe used.

In addition, in the embodiment, the phase is restored by using two pieces of detection data at different imaging distances. However, phase may be restored by using equal or more than three pieces of detection data at different imaging distances.

Figure 17:
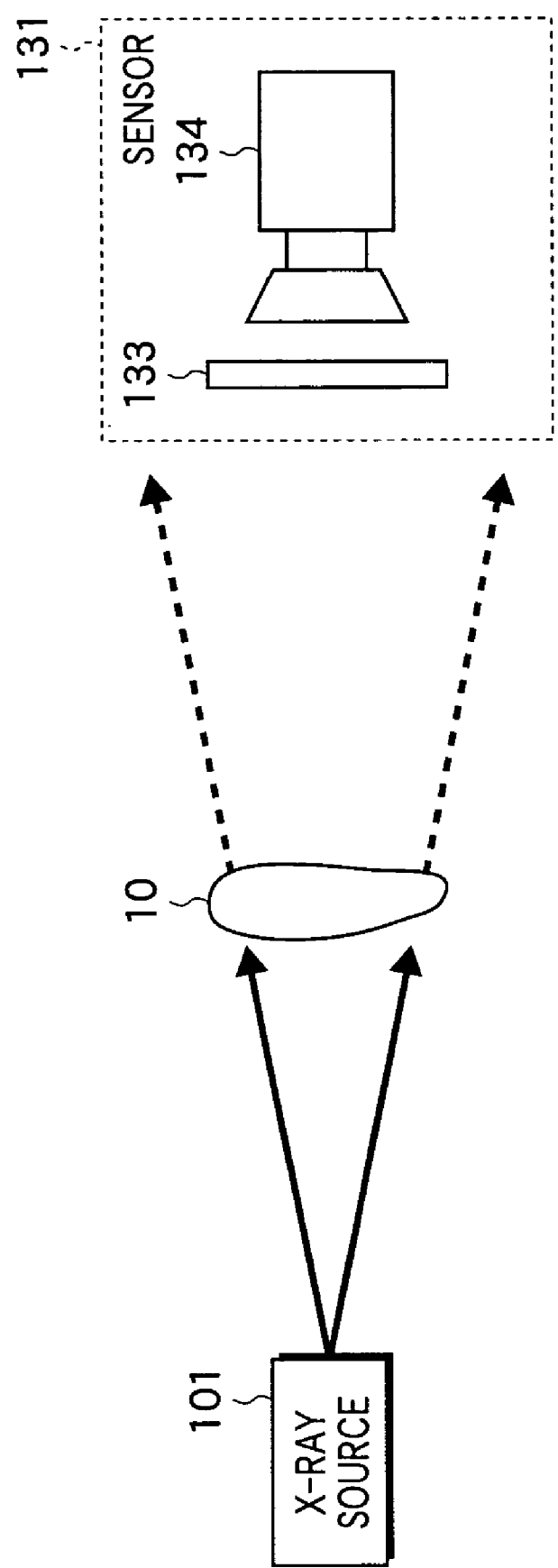
FIG. 17 is a diagram showing a constitution of the imaging unit when performing enlarging radiography.

Further, when performing radiation imaging, the X-ray transmitted through the object 10 may be enlarged and detected. For example, the fluorescence generated from the fluorescent screen 133 shown in FIG. 14 is enlarged by an optical system so as to be taken by the CCD camera 134. In this case, the effective pixel size (pixel size before enlarged) is used as $\Delta_x$ and $\Delta_y$ instead of the actual pixel size of the CCD. Alternatively, as shown in FIG. 17, by using a point source, etc. as the X-ray source, the X-ray may be detected in an enlarged scale, and also in this case, the effective pixel size is similarly used as $\Delta_x$ and $\Delta_y$.

Figure 18:
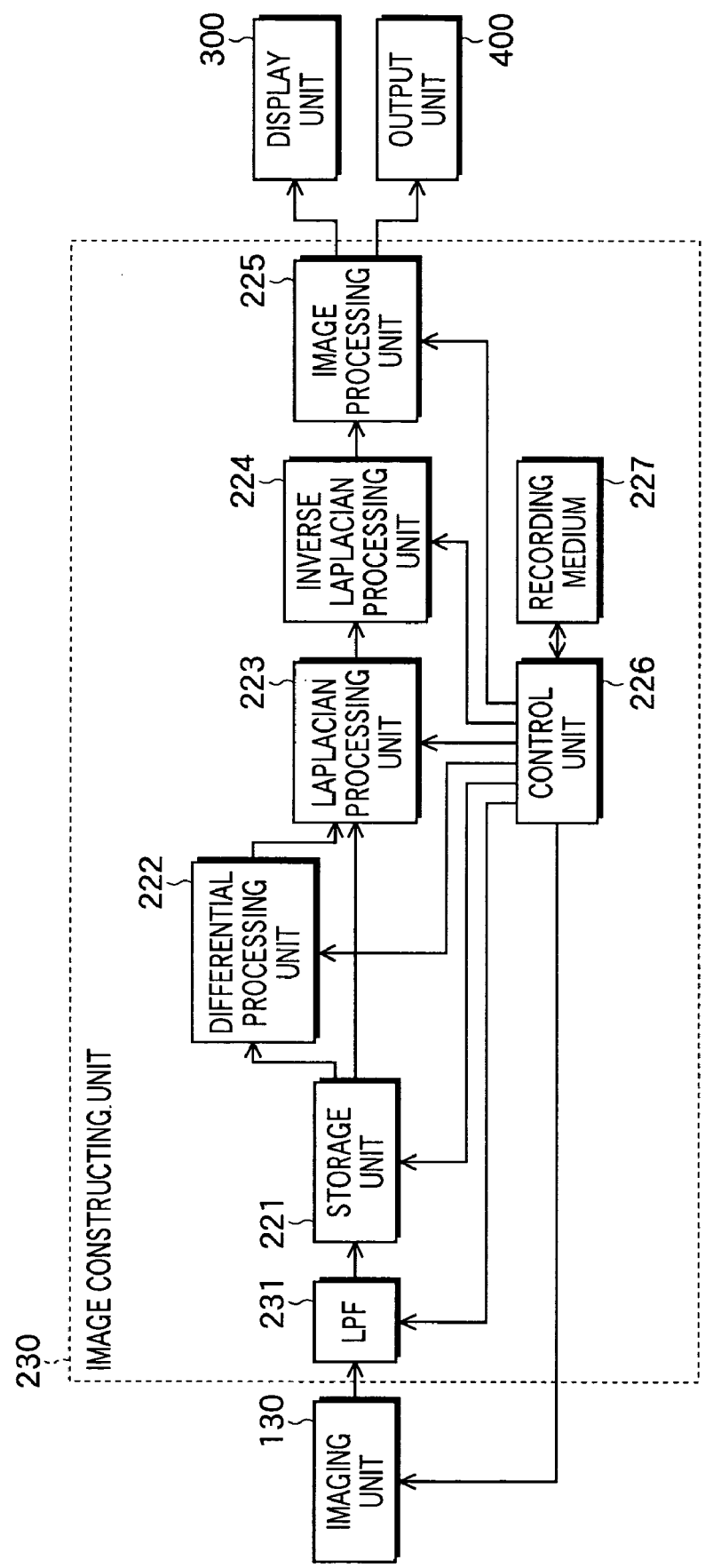
FIG. 18 is a block diagram showing a constitution of a phase information restoring apparatus according to a fourth embodiment of the present invention.

Next, a phase information restoring apparatus according to a fourth embodiment of the present invention will be described. FIG. 18 is a block diagram showing a constitution of the phase information restoring apparatus according to the fourth embodiment of the present invention.

As shown in FIG. 18, this phase information restoring apparatus includes an image constructing unit 230 instead of the image constructing unit 220 shown in FIG. 12, and other constitution is the same as that shown in FIG. 12. The image constructing unit 230 is constituted by further adding an LPF (low pass filter) 231 for performing low pass filter processing on the detection data outputted from the imaging unit 130 under the control of the control unit 226 and outputting the data to the storage unit 221 to the image constructing unit 220 shown in FIG. 12. In the embodiment, the low pass filter processing is performed by digital computation in order to suppress or eliminate high spatial frequency components.

Figure 19:
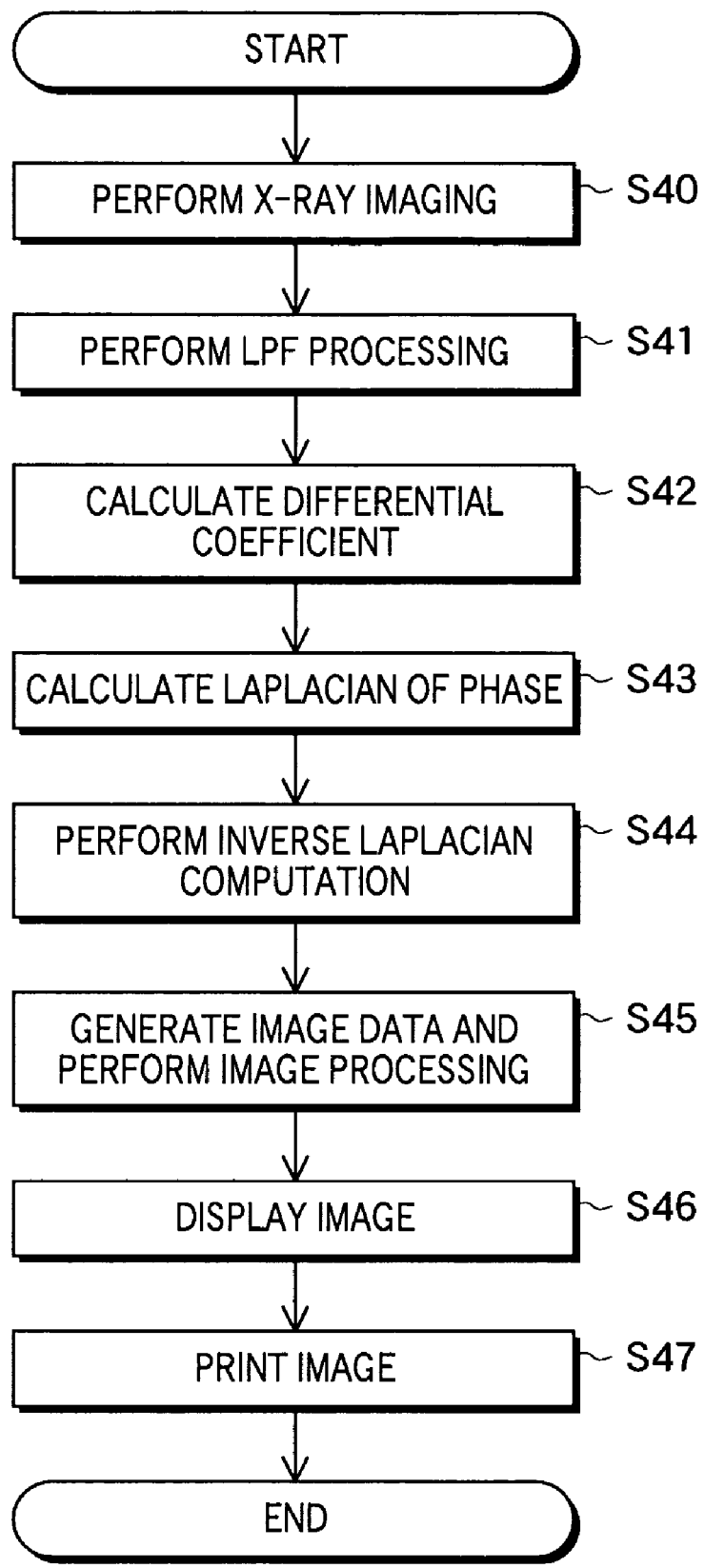
FIG. 19 is a flowchart showing a phase information restoring method according to the fourth embodiment of the present invention.

Next, a phase information restoring method according to the fourth embodiment of the present invention will be described by referring to FIGS. 13, 18, and 19. FIG. 19 is a flowchart showing the phase information restoring method according to the fourth embodiment of the present invention. In the embodiment, diffraction images are taken twice while changing the imaging distance and a visible image is constructed on the basis of the detection data representing image information on these diffraction images by using the phase-contrast method.

First, at step S40, X-ray imaging operation is performed. That is, as shown in FIG. 13, the object is positioned in a position where the distance from the X-ray source 101 is R, and the sensor driving unit 132 positions the sensor 131 in a position where the imaging distance is $z_1$ under the control of the control unit 226, an X-ray is applied to the object 10, thereby X-ray imaging is performed. Similarly, the X-ray imaging is performed by positioning the sensor 131 in a position where the imaging distance is $Z_2$.

By the X-ray imaging operation in step S40, the detection data I(x, y, $z_1$) and I(x, y, $z_2$) representing intensity of the diffraction X-ray entering the pixel (x, y) on the planes at respective imaging distances $z_1$ and $z_2$ are sequentially inputted to the image constructing unit 220. These detection data represent diffraction fringe image information on the planes at the respective imaging distances.

Next, at step S41, the LPF 231 performs low pass filter processing on the sequentially inputted detection data so as to obtain detection data $I_{LPF}(x, y, z_1)$ and $I_{LPF}(x, y, z_2)$ in which high spatial frequency components of the detection data are suppressed or eliminated. The detection data $I_{LPF}(x, y, z_1)$ and $I_{LPF}(x, y, z_2)$ obtained by the LPF 231 are sequentially stored in the storage unit 221.

Here, the region in which the high spatial frequency components are suppressed or eliminated by the LPF 231 is a region in which there is no signal because of the influence of blurs, as shown in FIG. 15. Therefore, in order to suppress or eliminate the spatial frequency components outside the triple sigma range, the spatial frequency components that satisfy $u > 3R/2\pi\sigma_x z$, $v > 3R/2\pi\sigma_y z$ may be suppressed or eliminated. Where, the longitudinal and lateral focal spot sizes are $\sigma_x$, $\sigma_y$, the distance between the X-ray source and the object is R, the imaging distance is z, and the spatial frequency components of x, y are u, v.

Next, at steps S42-S44, the image constructing unit 230 restores phase $\phi(x, y)$ in the position of the sensor on the basis of the detection data $I_{LPF}(x, y, z_1)$ and $I_{LPF}(x, y, z_2)$ stored in the storage unit 221.

First, at step S42, the differential processing unit 222 obtains a differential coefficient between the detection data $I_{LPF}(x, y, z_1)$ and the detection data $I_{LPF}(x, y, z_2)$ using the following equation (29).

$$\frac{\partial I(x, y, z)}{\partial z} = \frac{I_{LPF}(x, y, z_2) - I_{LPF}(x, y, z_1)}{z_2 - z_1} \quad (29)$$

Then, at step S43, the Laplacian processing unit 223 obtains Laplacian $f(x, y, z) = \nabla^2 \phi(x, y, z)$ of phase on the basis of the differential coefficient obtained at step S42 and the detection data stored in the storage unit 221 by using the following equation (30).

$$f(x, y, z) = -\frac{\kappa}{I_{LPF}(x, y, z_1)} \frac{\partial I(x, y, z)}{\partial z} \quad (30)$$

Here, in Eq. (30), although the differential coefficient is divided by the LPF processed detection data $I_{LPF}(x, y, z_1)$ at the shorter imaging distance, it may be divided by the LPF processed detection data $I_{LPF}(x, y, z_2)$ at the longer imaging distance.

Further, at step S44, the inverse Laplacian processing unit 224 obtains phase $\phi(x, y, z)$ by performing inverse Laplacian computation on the Laplacian $f(x, y, z) = \nabla^2 \phi(x, y, z)$ of the phase obtained at step S43. Note that the method of the inverse Laplacian computation is the same as that described in the first embodiment of the present invention.

Next, at step S45, the image processing unit 225 generates image data on the basis of the phase $\phi(x, y, z)$. That is, the image processing unit 225 converts the phase $\phi(x, y, z)$ in each pixel into data representing brightness and performs necessary image processing such as tone processing and interpolation processing.

Then, as far as necessary, at step S46, the display unit 300 displays a visible image on the basis of the image data on a display, and at step S47, the output unit 400 prints it out on a film, etc.

Next, a modified example of the phase information restoring apparatus according to the second to fourth embodiments of the present invention will be described. In the phase information restoring apparatus according to the second to fourth embodiments of the present invention, in stead of the sensor, a photo stimulable phosphor sheet (recording sheet) can be used as the screen used for recording image information similarly to that in the first embodiment.

Figure 20:
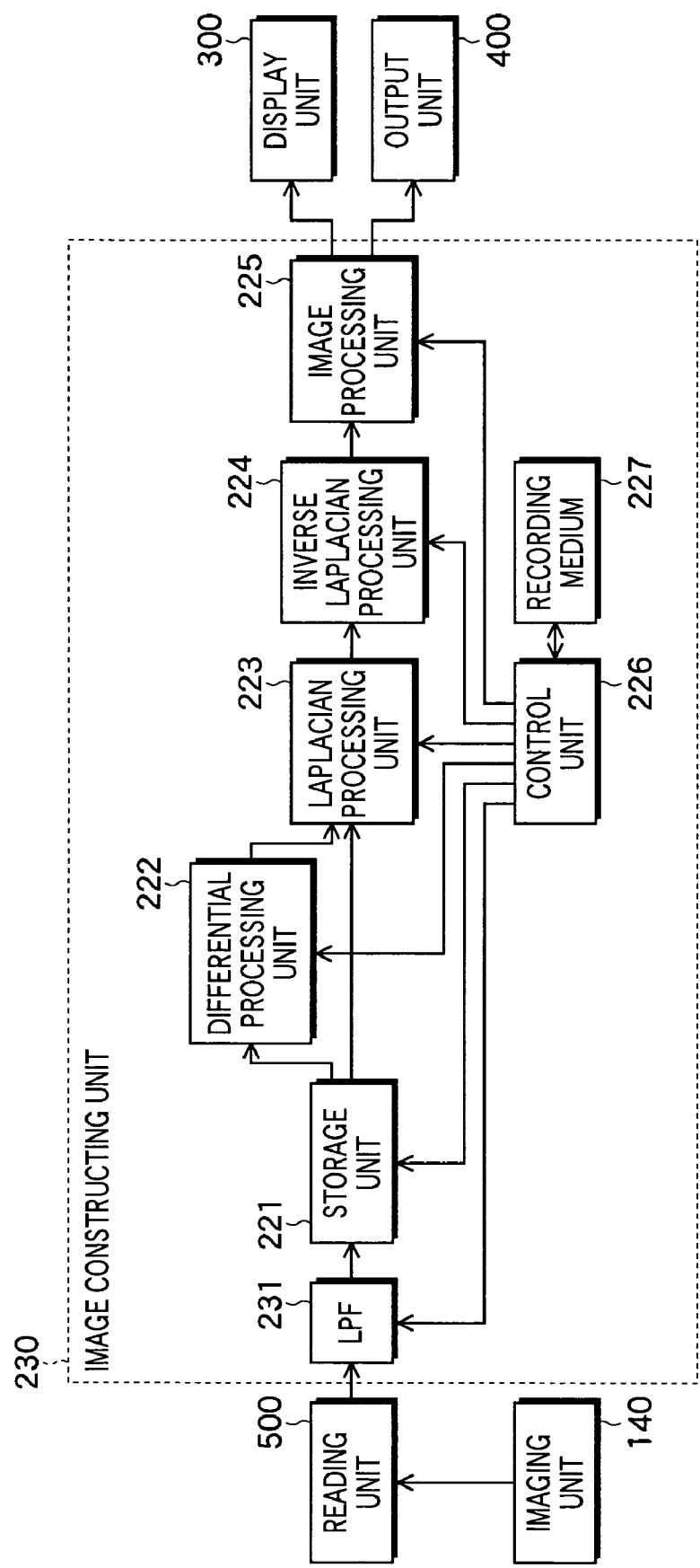
FIG. 20 is a block diagram showing a constitution of a modified example of the phase information restoring apparatus according to the fourth embodiment of the present invention.
Figure 21:
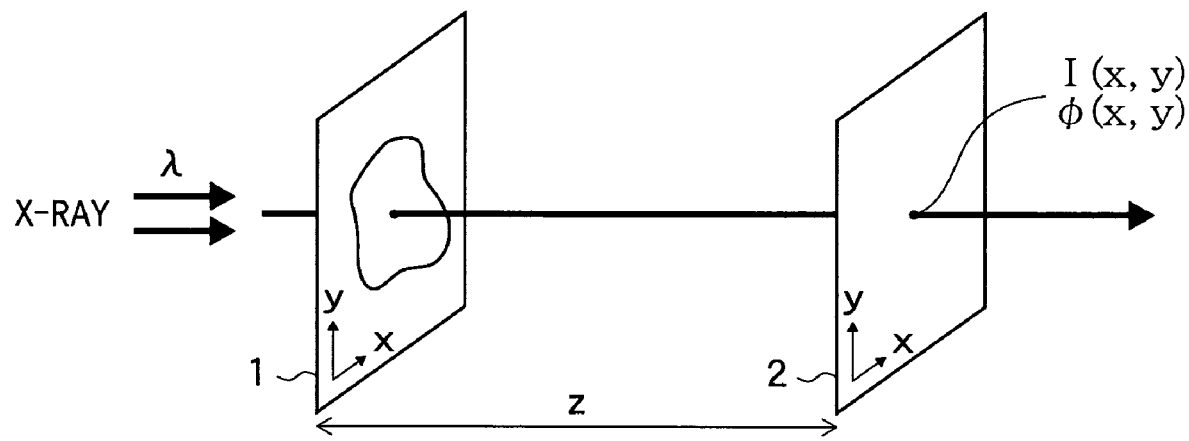
FIG. 21 is a diagram for explanation of a principle of phase restoration.

FIG. 20 shows a modified example of the phase information restoring apparatus according to the fourth embodiment of the present invention. This phase information restoring apparatus has an imaging unit 140 and a reading unit 500. Other constitution is the same as that of the phase information restoring apparatus shown in FIG. 18.

In the imaging unit 140, instead of the sensor 131 shown in FIG. 13, a photo stimulable phosphor sheet (recording sheet) is used. Further, the constitution and the operation of the reading unit 500 are similar to those described by referring to FIG. 8.

In the imaging unit 140, radiation imaging is performed by changing the imaging distance and using plural recording sheets. Further, in the reading unit 500, image information is read from the respective recording sheets, thereby detection data representing plural diffraction fringe images obtained at different imaging distances can be obtained. The image constructing unit 230 restores phase on the basis of this detection data and generates image data. The processing in the image constructing unit 230 is the same as that described by using FIG. 19.

As described above, according to the present invention, when constructing the radiation image of a living organism such as a human body by the phase-contrast method, the estimation accuracy of phase can be improved by using radiation with energy of high transmittance from 16 keV to 30 keV. In addition, according to the present invention, when constructing the radiation image of a living organism such as a human body by the phase-contrast method, the influence of noise can be reduced without increasing irradiation amount of the X-ray by eliminating the detection signals in the region where there is no signal because of blurs.

The invention claimed is:

1. A method of restoring phase information on a radiation transmitted through an object on the basis of detection data obtained by detecting intensity of the radiation transmitted though the object, said method comprising the steps of
   (a) obtaining plural sets of detection data respectively representing plural kinds of radiation image information on plural detection planes at different distances from the object by using a radiation having a predetermined wavelength with energy from 16 keV to 30 keV to detect intensity of the radiation on said plural detection planes;
   (b) obtaining a differential coefficient between said plural sets of detection data;

(c) calculating a Laplacian of phase on the basis of said differential coefficient and any one of said plural sets of detection data; and (d) performing inverse Laplacian computation on the Laplacian of phase to obtain the phase information.

2. A method according to claim 1, further comprising the step of generating image data on the basis of the phase information obtained at step (d).

3. An apparatus for restoring phase information on a radiation transmitted though an object on the basis of detection data obtained by detecting intensity of the radiation transmitted through the object, said apparatus comprising:

a radiation source for emitting a radiation having a predetermined wavelength with energy from 16 keV to 30 keV;

detecting means for detecting intensity of the radiation emitted from said radiation source and transmitted through the object so as to obtain detection data representing radiation image information;

driving means to be used for changing a distance between the object and said detecting means;

difference processing means for obtaining a differential coefficient between plural sets of detection data obtained by detecting intensity of the radiation at different distances;

Laplacian processing means for calculating a Laplacian of phase on the basis of said differential coefficient and any one of said plural sets of detection data; and Inverse Laplacian processing means for performing inverse Laplacian computation on the Laplacian of phase to obtain the phase information.

4. An apparatus according to claim 3, further comprising image constructing means for generating image data on the basis of the phase information obtained by said inverse Laplacian processing means.

* * * * *